US008626288B2

(12) United States Patent
Shuros et al.

(10) Patent No.: US 8,626,288 B2
(45) Date of Patent: Jan. 7, 2014

(54) SYSTEMS, DEVICES AND METHODS FOR MODULATING AUTONOMIC TONE

(75) Inventors: Allan C. Shuros, St. Paul, MN (US); Shantha Arcot-Krishnamurthy, Vadnais Heights, MN (US); Bruce H. KenKnight, Maple Grove, MN (US); Douglas R. Daum, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1190 days.

(21) Appl. No.: 12/397,464

(22) Filed: Mar. 4, 2009

(65) Prior Publication Data
US 2009/0234406 A1 Sep. 17, 2009

Related U.S. Application Data

(60) Provisional application No. 61/036,424, filed on Mar. 13, 2008.

(51) Int. Cl.
*A61N 1/368* (2006.01)

(52) U.S. Cl.
USPC .............................................. 607/9

(58) Field of Classification Search
USPC ................................. 607/9, 17, 18
See application file for complete search history.

(56) References Cited

U.S. PATENT DOCUMENTS

| | | | |
|---|---|---|---|
| 5,203,326 A | 4/1993 | Collins | |
| 6,532,388 B1 | 3/2003 | Hill et al. | |
| 6,571,121 B2 * | 5/2003 | Schroeppel et al. | 600/515 |
| 7,123,961 B1 * | 10/2006 | Kroll et al. | 607/9 |
| 7,260,431 B2 | 8/2007 | Libbus et al. | |

(Continued)

FOREIGN PATENT DOCUMENTS

| | | |
|---|---|---|
| JP | 2007-537840 A | 12/2007 |
| WO | WO-2006/121842 A2 | 11/2006 |
| WO | WO-2009114096 A1 | 9/2009 |

OTHER PUBLICATIONS

Simms, Annabel E. et al., "Hierarchical Recruitment of the Sympathetic and Parasympathetic Limbs of the Baroreflex in Normotensive and Spontaneously Hypertensve Rats," Joural of Physiology 579.2 (2007) 473-483.*

(Continued)

Primary Examiner — Christopher D Koharski
Assistant Examiner — Frances Oropeza
(74) Attorney, Agent, or Firm — Schwegman Lundberg & Woessner, P.A.

(57) ABSTRACT

Various embodiments intermittently deliver a sympathetic stimulus, including deliver a sequence of stress-inducing pacing pulses adapted to increase sympathetic tone during the stress-inducing pacing. The stress-inducing pacing results in a parasympathetic reflex after the sequence of stress-inducing pacing. The embodiment further delivers neural stimulation to elicit a parasympathetic response or a sympathetic response in a coordinated manner with respect to the sequence of stress-inducing pacing pulses. The neural stimulation is timed to elicit the parasympathetic response after the sequence of stress-inducing pacing pulses and concurrent with at least a portion of the parasympathetic reflex to the sequence of stress-inducing pacing to enhance a parasympathetic effect of the parasympathetic reflex, or to elicit the sympathetic response during the sequence of stress-inducing pulses to provide a larger sympathetic stimulus, resulting in an enhanced parasympathetic reflex in response to the large sympathetic stimulus.

7 Claims, 17 Drawing Sheets

(56) References Cited

U.S. PATENT DOCUMENTS

| | | | |
|---|---|---|---|
| 7,805,193 | B2 | 9/2010 | Libbus et al. |
| 2004/0172075 | A1 | 9/2004 | Shafer et al. |
| 2004/0199210 | A1 | 10/2004 | Shelchuk |
| 2004/0249416 | A1* | 12/2004 | Yun et al. ............... 607/2 |
| 2005/0261741 | A1 | 11/2005 | Libbus et al. |
| 2006/0206154 | A1* | 9/2006 | Moffitt et al. ............. 607/9 |
| 2006/0206159 | A1 | 9/2006 | Moffitt et al. |
| 2006/0253156 | A1 | 11/2006 | Pastore et al. |
| 2007/0142864 | A1 | 6/2007 | Libbus et al. |
| 2007/0288070 | A1 | 12/2007 | Libbus et al. |

OTHER PUBLICATIONS

"International Application Serial No. PCT/US2009/001374, International Search Report mailed Jul. 2, 2009", 3 pgs.

"International Application Serial No. PCT/US2009/001374, Written Opinion mailed Jul. 2, 2009", 8 pgs.

Adamopoulos, S., "Effects of pulsed β-stimulant therapy on β-adrenoceptors and chronotropic responsiveness in chronic heart failure.", *Lancet*, 345(8946), (Feb. 11, 1995), 344-349.

Coats, A. J., et al., "Controlled trial of physical training in chronic heart failure. Exercise performance, hemodynamics, ventilation, and autonomic function", *Circulation*, 85(6), (1992), 2119-2131.

Leier, C. V., "Drug-induced conditioning in congestive heart failure.", *Circulation*, 65(7), (Jun. 1982), 1382-1387.

Liang, C., "Conditioning effects of chronic infusions of dobutamine. Comparison with exercise training.", *Journal of Clinical Investigation*, 64(2), (Aug. 1979), 613-619.

Myers, J., et al., "Exercise Training and Myocardial Remodeling in Patients with Reduced Ventricular Function: One-Year Follow-up with Magnetic Resonance Imaging", *American Heart Journal*, 139(2), (2000), 252-261.

"European Application Serial No. 09720923.3, Office Action mailed Nov. 9, 2010", 2 pgs.

"European Application Serial No. 09720923.3, Response filed Dec. 15, 2010 to Office Action mailed Nov. 9, 2010", 11 pgs.

"International Application Serial No. PCT/US2009/001374, International Preliminary Report on Patentability mailed Sep. 23, 2010", 9 pgs.

"Japanese Application Serial No. 2010-550676, Office Action mailed Jun. 26, 2012", With English Translation, 3 pgs.

"Japanese Application Serial No. 2010-550676, Response filed Sep. 24, 2012 to Office Action mailed Jun. 26, 2012", 3 pgs.

\* cited by examiner

SYSTEMS, DEVICES AND METHODS FOR MODULATING AUTONOMIC TONE

CROSS-REFERENCE TO RELATED APPLICATION

This application claims the benefit of U.S. Provisional Application No. 61/036,424, filed on Mar. 13, 2008, under 35 U.S.C. §119(e), which is hereby incorporated by reference.

TECHNICAL FIELD

This application relates generally to medical devices and, more particularly, to systems, devices and methods for modulating autonomic tone.

BACKGROUND

Heart disease such as myocardial infarction and/or heart failure can cause adverse ventricular remodeling and an imbalance in autonomic tone favoring sympathetic activity over parasympathetic tone. During heart disease, the compromised ventricles may be less than capable of maintaining normal cardiac output. As a result, the body compensates for the reduced cardiac output by increasing sympathetic tone and suppressing parasympathetic activity, resulting in increased heart rate, myocardial contractility and blood volume. This mechanism is acutely beneficial, but has a long-term deleterious effect.

It has been shown experimentally that intermittent stress such as exercise, dobutamine infusion, myocardial pacing, or external counterpulsation provides beneficial conditioning effects for the heart and body. Intermittent stress (e.g. exercise) improved the imbalance in the autonomic tone, as the autonomic tone trended from a predominantly sympathetic tendency toward a desired autonomic balance between the sympathetic and parasympathetic systems. For example, intensive exercise training in patients with reduced ventricular function has been shown to result in a significant improvement in exercise capacity (increased $O_2$ uptake, maximum minute ventilation, $CO_2$ production, exercise time and watts), with no deleterious effects on left ventricular volume, function or wall thickness. A potential mechanism for the benefit may be that these short intervals of stress increase sympathetic tone and cause a reflexive increase in parasympathetic tone after the stress is discontinued.

Intermittent sympathomimetic stimulation in animals with dobutamine produces benefits analogous to those of physical conditioning. In a pilot clinical study, patients with stable moderate severe HF (EF=23%) who received dobutamine therapy (30 min/day, 4 days/week, 3 weeks) experienced the following benefits: increased exercise tolerance; improved heart rate variability; lowered peripheral vascular resistance; and reduced plasma noradrenaline.

Neural (eg. vagus) stimulation has been shown to provide benefit to heart disease animal models. This therapy may also provide benefit by restoring balance to the autonomic tone. The vagus nerve of the animals in these models had both sympathetic and parasympathetic fibers.

SUMMARY

Various system embodiments comprise a myocardial stimulator, a neural stimulator and a controller connected to the myocardial stimulator and to the neural stimulator. The myocardial stimulator is adapted to deliver pacing pulses through at least one electrode to provide cardiac pacing. The neural stimulator is adapted to deliver neural stimulation through at least one electrode to at least one desired neural target to elicit at least one of a parasympathetic response or a sympathetic response. The controller is adapted to intermittently deliver a sympathetic stimulus using the myocardial stimulator. The sympathetic stimulus includes a sequence of stress-inducing pacing pulses adapted to increase sympathetic tone during the stress-inducing pacing. The sequence of stress-inducing pacing results in a parasympathetic reflex after the sequence of stress-inducing pacing is discontinued. The controller is adapted to implement a neural stimulation therapy using the neural stimulator, and coordinate timing between the sequence of stress-inducing pacing pulses and the neural stimulation to enhance the parasympathetic reflex after the sequence of stress-inducing pacing. The controller is adapted to time neural stimulation to elicit at least one of: the parasympathetic response after the sequence of stress-inducing pacing pulses and concurrent with at least a portion of the parasympathetic reflex to the sequence of stress-inducing pacing to enhance a parasympathetic effect of the parasympathetic reflex; or the sympathetic response during the sequence of stress-inducing pulses to provide a larger sympathetic stimulus, resulting in an enhanced parasympathetic reflex in response to the large sympathetic stimulus.

Various system embodiments comprise means for intermittently delivering a sympathetic stimulus, including means for delivering a sequence of stress-inducing pacing pulses adapted to increase sympathetic tone during the stress-inducing pacing. The sequence of stress-inducing pacing results in a parasympathetic reflex after the sequence of stress-inducing pacing. The system embodiment further includes means for delivering neural stimulation to elicit a parasympathetic response or a sympathetic response in a coordinated manner with respect to the sequence of stress-inducing pacing pulses. The neural stimulation is timed to elicit the parasympathetic response after the sequence of stress-inducing pacing pulses and concurrent with at least a portion of the parasympathetic reflex to the sequence of stress-inducing pacing to enhance a parasympathetic effect of the parasympathetic reflex, or to elicit the sympathetic response during the sequence of stress-inducing pulses to provide a larger sympathetic stimulus, resulting in an enhanced parasympathetic reflex in response to the large sympathetic stimulus.

According to various method embodiments, a sympathetic stimulus is intermittently delivered. Delivering the sympathetic stimulus includes delivering a sequence of stress-inducing pacing pulses adapted to increase sympathetic tone during the stress-inducing pacing. The sequence of stress-inducing pacing results in a parasympathetic reflex after the sequence of stress-inducing pacing. Neural stimulation is delivered to elicit a parasympathetic response in a coordinated manner with respect to the sequence of stress-inducing pacing pulses to enhance the parasympathetic reflex after the sequence of stress-inducing pacing. Delivering the neural stimulation includes timing the neural stimulation to elicit the parasympathetic response after the sequence of stress-inducing pacing pulses and concurrent with at least a portion of the parasympathetic reflex to the sequence of stress-inducing pacing to enhance a parasympathetic effect of the parasympathetic reflex.

According to various method embodiments, a sympathetic stimulus is intermittently delivered. Delivering the sympathetic stimulus includes delivering a sequence of stress-inducing pacing pulses adapted to increase sympathetic tone during the stress-inducing pacing. The sequence of stress-inducing pacing results in a parasympathetic reflex after the sequence of stress-inducing pacing. Neural stimulation is delivered to elicit a sympathetic response in a coordinated manner with respect to the sequence of stress-inducing pacing pulses to enhance the parasympathetic reflex after the sequence of stress-inducing pacing. Delivering the neural stimulation includes timing the neural stimulation to elicit the sympathetic response during the sequence of stress-inducing pulses to provide a larger sympathetic stimulus, resulting in an enhanced parasympathetic reflex in response to the larger sympathetic stimulus.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

Figure 1:
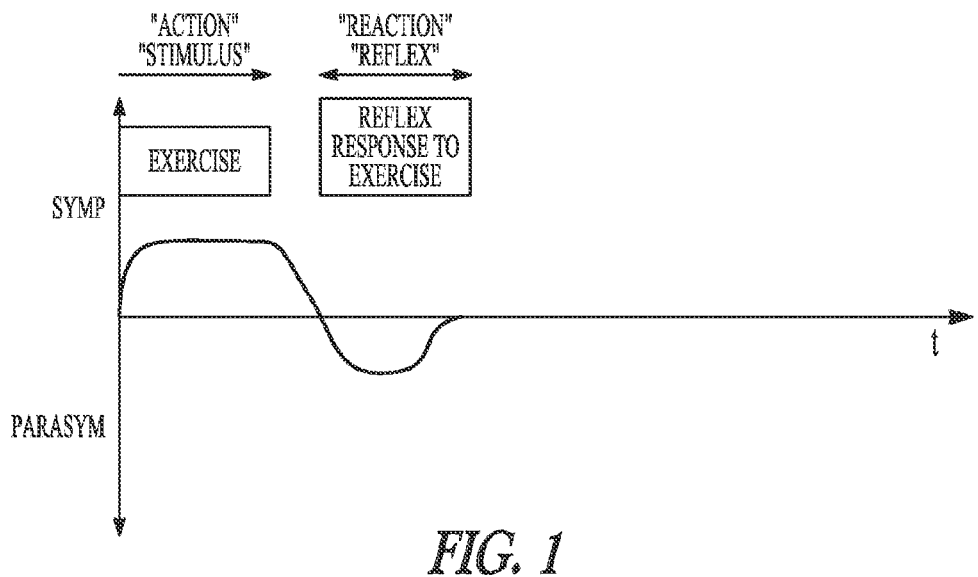
FIG. 1 illustrates the autonomic response to a period of exercise.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

This disclosure describes a system for modulating autonomic tone for prophylactic and/or therapeutic treatment of diseases. Unlike the animal models used to show a benefit of vagus nerve stimulation for heart disease, whose vagus nerve had both parasympathetic and sympathetic fibers, humans have entirely parasympathetic fibers in the vagus nerve, such that the vagus stimulation does not provide a sympathetic stimulation component. The present subject matter provides the ability to modulate both parasympathetic and sympathetic tone. The modulation of the sympathetic component is achieved by inducing cardiac stress with cardiac protection pacing therapy, and the modulation of the parasympathetic component is achieved with neural stimulation.

Various embodiments provide an implantable medical device system for modulating autonomic tone to improve the autonomic balance of the parasympathetic and sympathetic nervous systems. The system is capable of delivering myocardial pacing in a manner that intentionally stresses the heart (e.g. faster rate and/or AV delays compared to the intrinsic cardiac activity) to modulate a sympathetic component, and neural stimulation to modulate a parasympathetic component. Some embodiments deliver neural stimulation to further modulate a sympathetic component to enhance the sympathetic effect of the cardiac protection pacing therapy. The duty cycles, pulses, duration, energy, etc. of the neural stimulation can be modulated in some embodiments. Some embodiments perform alternate stimulation mode switching to enhance vagal surge effects (sympathetic stimulation followed by parasympathetic stimulation). Some embodiments perform both sympathetic and parasympathetic stimulation simultaneously. Physiological parameters such as heart rate variability (HRV), heart rate turbulence (HRT), neurotransmitter levels, heart rate, blood pressure, respiration and activity may be used to titrate the autonomic balance therapy.

The modulation of autonomic tone to improve the autonomic balance for the heart may be referred to as a cardiac or myocardial conditioning therapy. Cardiac conditioning therapy may be used in a heart failure therapy, a hypertension therapy, or a post-MI therapy (treatment for remodeling).

Physiology

Provided below is a brief discussion of the nervous system and some diseases capable of being treated using the present subject matter. This discussion is believed to assist a reader in understanding the disclosed subject matter.

Nervous System

The autonomic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system. Afferent nerves convey impulses toward a nerve center, and efferent nerves convey impulses away from a nerve center.

The heart rate and force is increased when the sympathetic nervous system is stimulated, and is decreased when the sympathetic nervous system is inhibited (the parasympathetic nervous system is stimulated). Cardiac rate, contractility, and excitability are known to be modulated by centrally mediated reflex pathways. Baroreceptors and chemoreceptors in the heart, great vessels, and lungs, transmit cardiac activity through vagal and sympathetic afferent fibers to the central nervous system. Activation of sympathetic afferents triggers reflex sympathetic activation, parasympathetic inhibition, vasoconstriction, and tachycardia. In contrast, parasympathetic activation results in bradycardia, vasodilation, and inhibition of vasopressin release. Among many other factors, decreased parasympathetic or vagal tone or increased sympathetic tone is associated with various arrhythmias genesis, including ventricular tachycardia and atrial fibrillation.

Baroreflex is a reflex triggered by stimulation of a baroreceptor. A baroreceptor includes any sensor of pressure changes, such as sensory nerve endings in the wall of the auricles of the heart, vena cava, aortic arch and carotid sinus, that is sensitive to stretching of the wall resulting from increased pressure from within, and that functions as the receptor of the central reflex mechanism that tends to reduce that pressure. Clusters of nerve cells can be referred to as autonomic ganglia. These nerve cells can also be electrically stimulated to induce a baroreflex, which inhibits the sympathetic nerve activity and stimulates parasympathetic nerve activity. Autonomic ganglia thus forms part of a baroreflex pathway. Afferent nerve trunks, such as the vagus, aortic and carotid nerves, leading from the sensory nerve endings also form part of a baroreflex pathway. Stimulating a baroreflex pathway and/or baroreceptors inhibits sympathetic nerve activity (stimulates the parasympathetic nervous system) and reduces systemic arterial pressure by decreasing peripheral vascular resistance and cardiac contractility. Baroreceptors are naturally stimulated by internal pressure and the stretching of vessel wall (e.g. arterial wall).

Stimulating the sympathetic and parasympathetic nervous systems can have effects other than heart rate and blood pressure. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, and increases digestion in the small intention, increases urine secretion, and contracts the wall and relaxes the sphincter of the bladder. The functions associated with the sympathetic and parasympathetic nervous systems are many and can be complexly integrated with each other.

Neural stimulation can be used to stimulate nerve traffic or inhibit nerve traffic. An example of neural stimulation to stimulate nerve traffic is a lower frequency signal (e.g. within a range on the order of 20 Hz to 50 Hz). An example of neural stimulation to inhibit nerve traffic is a higher frequency signal (e.g. within a range on the order of 120 Hz to 150 Hz). Other methods for stimulating and inhibiting nerve traffic have been proposed. According to various embodiments of the present subject matter, sympathetic neural targets include, but are not limited to, a peroneal nerve, a sympathetic column in a spinal cord, and cardiac post-ganglionic sympathetic neurons. According to various embodiments of the present subject matter, parasympathetic neural targets include, but are not limited to, a vagus nerve, a baroreceptor, and a cardiac fat pad. Neural stimulation can be selectively delivered to afferent neural pathways, selectively delivered to efferent neural pathways, or delivered to both afferent and efferent neural pathways. For example, some embodiments selectively stimulate or inhibit only parasympathetic afferents or only parasympathetic efferents, and some embodiments selectively stimulate or inhibit sympathetic afferents or efferents.

Diseases

The present subject matter can be used to prophylactically or therapeutically treat various diseases by modulating autonomic tone. Examples of such diseases or conditions include hypertension, cardiac remodeling, and heart failure.

Hypertension is a cause of heart disease and other related cardiac co-morbidities. Hypertension occurs when blood vessels constrict. As a result, the heart works harder to maintain flow at a higher blood pressure, which can contribute to heart failure. Hypertension generally relates to high blood pressure, such as a transitory or sustained elevation of systemic arterial blood pressure to a level that is likely to induce cardiovascular damage or other adverse consequences. Hypertension has been defined as a systolic blood pressure above 140 mm Hg or a diastolic blood pressure above 90 mm Hg. Consequences of uncontrolled hypertension include, but are not limited to, retinal vascular disease and stroke, left ventricular hypertrophy and failure, myocardial infarction, dissecting aneurysm, and renovascular disease. A large segment of the general population, as well as a large segment of patients implanted with pacemakers or defibrillators, suffer from hypertension. The long term mortality as well as the quality of life can be improved for this population if blood pressure and hypertension can be reduced. Many patients who suffer from hypertension do not respond to treatment, such as treatments related to lifestyle changes and hypertension drugs.

Following myocardial infarction (MI) or other cause of decreased cardiac output, a complex remodeling process of the ventricles occurs that involves structural, biochemical, neurohormonal, and electrophysiologic factors. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation. As the heart begins to dilate, afferent baroreceptor and cardiopulmonary receptor signals are sent to the vasomotor central nervous system control center, which responds with hormonal secretion and sympathetic discharge. It is the combination of hemodynamic, sympathetic nervous system and hormonal alterations (such as presence or absence of angiotensin converting enzyme (ACE) activity) that ultimately account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction (decompensation). It has been shown that the extent of ventricular remodeling is positively correlated with increased mortality in post-MI and heart failure patients.

Heart failure refers to a clinical syndrome in which cardiac function causes a below normal cardiac output that can fall below a level adequate to meet the metabolic demand of peripheral tissues. Heart failure may present itself as congestive heart failure (CHF) due to the accompanying venous and pulmonary congestion. Heart failure can be due to a variety of etiologies such as ischemic heart disease. Heart failure patients have reduced autonomic balance, which is associated with LV dysfunction and increased mortality. Modulation of the sympathetic and parasympathetic nervous systems has potential clinical benefit in preventing remodeling and death in heart failure and post-MI patients. Direct electrical stimulation can activate the baroreflex, inducing a reduction of sympathetic nerve activity and reducing blood pressure by decreasing vascular resistance. Sympathetic inhibition and parasympathetic activation have been associated with reduced arrhythmia vulnerability following a myocardial infarction, presumably by increasing collateral perfusion of the acutely ischemic myocardium and decreasing myocardial damage.

CPPT

The sinoatrial (SA) node generates electrical impulses that propagate through an electrical conduction system to various regions of the heart to excite the myocardial tissues of these regions. An intrinsic heart rhythm may be a normal rhythm or an abnormal rhythm. Coordinated delays in the propagations of the electrical impulses in a normal electrical conduction system causes the various portions of the heart to contract in synchrony. Synchrony, as used herein, indicates a coordinated contraction of the various portions of the heart to result in efficient pumping functions. Synchrony does not indicate that all of the portions of the heart contract at the same time.

Abnormal electrical conduction and/or deteriorated myocardial tissue cause asynchrony (no coordinated timing) between the various portions of the heart, which result in inefficient pumping functions. The present subject matter relates to systems, devices and methods for modulating autonomic tone. The present subject matter uses cardiac protective pacing therapy (CPPT) and neural stimulation to provide a cardiac conditioning therapy to improve autonomic balance, and thus improve the health of the heart. CPPT is an intermittent pacing therapy that paces the heart in such a manner as to intentionally stress the heart during intermittent periods. When the heart is stressed with CPPT, the heart is paced to force the heart to work harder in comparison to a time when CPPT is not applied to the heart. The paced heart works harder in local regions of the heart away from a site where the stress-inducing pacing pulses are delivered. For example, a stressed heart may be paced to beat faster and/or more asynchronous (less coordinated). By way of example and not limitation, various CPPT embodiments increase the pacing rate for the right atrium, increase the pacing rate for the right ventricle, shorten an AV delay, and/or lengthen the VV delay. Increasing the intensity of the CPPT may involve further increasing the pacing rate of the right atrium or right ventricle, further shortening the AV delay to be more different from the intrinsic rate without CPPT, and/or further lengthening of the VV delay to be more different from the intrinsic rate without CPPT. Decreasing the intensity of the CPPT may involve reducing the pacing rate of the right atrium or right ventricle closer to the intrinsic rate, may involve increasing the AV delay closer to the intrinsic AV delay, and/or may involve shortening the VV delay closer to the intrinsic VV delay (whether or not the intrinsic rhythm is normal or abnormal). Delivering CPPT with higher intensity corresponds to increasing the sympathetic response during the CPPT.

Autonomic Balance Indicator (ABI)

An ABI can be used to provide closed-loop control of the therapy to adjust autonomic tone. Various embodiments assess ABI using one or various combinations of parameters, such as heart rate variability (HRV), heart rate turbulence (HRT), electrogram features, activity, respiration, and pulmonary artery pressure. These parameters are briefly discussed below. Various embodiments provide closed loop control of the treatment using ABI.

HRV is one technique that has been proposed to assess autonomic balance. HRV relates to the regulation of the sinoatrial node, the natural pacemaker of the heart by the sympathetic and parasympathetic branches of the autonomic nervous system. An HRV assessment is based on the assumption that the beat-to-beat fluctuations in the rhythm of the heart provide us with an indirect measure of heart health, as defined by the degree of balance in sympathetic and vagus nerve activity.

The time interval between intrinsic ventricular heart contractions changes in response to the body's metabolic need for a change in heart rate and the amount of blood pumped through the circulatory system. For example, during a period of exercise or other activity, a person's intrinsic heart rate will generally increase over a time period of several or many heartbeats. However, even on a beat-to-beat basis, that is, from one heart beat to the next, and without exercise, the time interval between intrinsic heart contractions varies in a normal person. These beat-to-beat variations in intrinsic heart rate are the result of proper regulation by the autonomic nervous system of blood pressure and cardiac output; the absence of such variations indicates a possible deficiency in the regulation being provided by the autonomic nervous system. One method for analyzing HRV involves detecting intrinsic ventricular contractions, and recording the time intervals between these contractions, referred to as the R-R intervals, after filtering out any ectopic contractions (ventricular contractions that are not the result of a normal sinus rhythm). This signal of R-R intervals is typically transformed into the frequency-domain, such as by using fast Fourier transform ("FFT") techniques, so that its spectral frequency components can be analyzed and divided into low and high frequency bands. For example, the low frequency (LF) band can correspond to a frequency ("f") range $0.04 Hz \leq f < 0.15 Hz$, and the high frequency (HF) band can correspond to a frequency range $0.15 Hz \leq f \leq 0.40 Hz$. The HF band of the R-R interval signal is influenced only by the parasympathetic/vagal component of the autonomic nervous system. The LF band of the R-R interval signal is influenced by both the sympathetic and parasympathetic components of the autonomic nervous system. Consequently, the ratio LF/HF is regarded as a good indication of the autonomic balance between sympathetic and parasympathetic/vagal components of the autonomic nervous system. An increase in the LF/HF ratio indicates an increased predominance of the sympathetic component, and a decrease in the LF/HF ratio indicates an increased predominance of the parasympathetic component. For a particular heart rate, the LF/HF ratio is regarded as an indication of patient wellness, with a lower LF/HF ratio indicating a more positive state of cardiovascular health. A spectral analysis of the frequency components of the R-R interval signal can be performed using a FFT (or other parametric transformation, such as autoregression) technique from the time domain into the frequency domain. Such calculations require significant amounts of data storage and processing capabilities. Additionally, such transformation calculations increase power consumption, and shorten the time during which the implanted battery-powered device can be used before its replacement is required.

One example of an HRV parameter is SDANN (standard deviation of averaged NN intervals), which represents the standard deviation of the means of all the successive 5 minutes segments contained in a whole recording. Other HRV parameters can be used.

HRT is the physiological response of the sinus node to a premature ventricular contraction (PVC), consisting of a short initial heart rate acceleration followed by a heart rate deceleration. HRT has been shown to be an index of autonomic function, closely correlated to HRV. HRT is believed to be an autonomic baroreflex. The PVC causes a brief disturbance of the arterial blood pressure (low amplitude of the premature beat, high amplitude of the ensuing normal beat). This fleeting change is registered immediately with an instantaneous response in the form of HRT if the autonomic system is healthy, but is either weakened or missing if the autonomic system is impaired.

By way of example and not limitation, it has been proposed to quantify HRT using Turbulence Onset (TO) and Turbulence Slope (TS). TO refers to the difference between the heart rate immediately before and after a PVC, and can be expressed as a percentage. For example, if two beats are evaluated before and after the PVC, TO can be expressed as:

$$TO\ \% = \frac{(RR_{+1} + RR_{+2}) - (RR_{-2} + RR_{-1})}{(RR_{-2} + RR_{-1})} * 100.$$

$RR_{-2}$ and $RR_{-1}$ are the first two normal intervals preceding the PVC and $RR_{+1}$ and $RR_{+2}$ are the first two normal intervals following the PVC. In various embodiments, TO is determined for each individual PVC, and then the average value of all individual measurements is determined. However, TO does not have to be averaged over many measurements, but can be based on one PVC event. Positive TO values indicate deceleration of the sinus rhythm, and negative values indicate acceleration of the sinus rhythm. The number of R-R intervals analyzed before and after the PVC can be adjusted according to a desired application. TS, for example, can be calculated as the steepest slope of linear regression for each sequence of five R-R intervals. In various embodiments, the TS calculations are based on the averaged tachogram and expressed in milliseconds per RR interval. However, TS can be determined without averaging. The number of R-R intervals in a sequence used to determine a linear regression in the TS calculation also can be adjusted according to a desired application.

Rules or criteria can be provided for use to select PVCs and for use in selecting valid RR intervals before and after the PVCs. A PVC event can be defined by an R-R interval in some interval range that is shorter than a previous interval by some time or percentage, or it can be defined by an R-R interval without an intervening P-wave (atrial event) if the atrial events are measured. Various embodiments select PVCs only if the contraction occurs at a certain range from the preceding contraction and if the contraction occurs within a certain range from a subsequent contraction. For example, various embodiments limit the HRT calculations to PVCs with a minimum prematurity of 20% and a post-extrasystole interval which is at least 20% longer than the normal interval. Additionally, pre-PVC R-R and post-PVC R-R intervals are considered to be valid if they satisfy the condition that none the of the beats are PVCs. One HRT process, for example, excludes RR intervals that are less than a first time duration, that are longer than a second time duration, that differ from a preceding interval by more than a third time duration, or that differ from a reference interval by a predetermined amount time duration or percentage. In an embodiment of such an HRT process with specific values, RR intervals are excluded if they are less than 300 ms, are more than 2000 ms, differ from a preceding interval by more than 200 ms, or differ by more than 20% from the mean of the last five sinus intervals.

Various embodiments of the present subject matter provide programmable parameters, such as any of the parameters identified above, for use in selecting PVCs and for use in selecting valid RR intervals before and after the PVCs.

The neural stimulation device that incorporates this technique for assessing autonomic balance can be used to provide either parasympathetic stimulation or inhibition or sympathetic stimulation or inhibition. Various device embodiments include means for pacing a ventricle, such as at least one ventricular pacing lead. To measure autonomic balance for closed-loop therapy titration, the device intermittently introduces or senses a PVC, and measures the resulting HRT, as described above.

Benefits of using HRT to monitor autonomic balance include the ability to measure autonomic balance at a single moment in time. Additionally, unlike the measurement of HRV, HRT assessment can be performed in patients with frequent atrial pacing. Further, HRT analysis provides for a simple, non-processor-intensive measurement of autonomic balance. Thus, data processing, data storage, and data flow are relatively small, resulting in a device with less cost and less power consumption. Also, HRT assessment is faster than HRV, requiring much less R-R data. HRT allows assessment over short recording periods similar in duration to typical neural stimulation burst durations, such as on the order of tens of seconds, for example.

Various embodiments extract various ECG features to provide an ABI. Examples of such features include heart rate, which can be used to form HRV, and heart rate turbulence. Other features can be extracted from the ECG, and one or various combinations of these features can be used to provide an ABI. Various embodiments provide blood pressure to provide an ABI. For example, some embodiment sense pulmonary artery blood pressure.

Activity sensors can be used to assess the activity of the patient. Sympathetic activity naturally increases in an active patient, and decreases in an inactive patient. Thus, activity sensors can provide a contextual measurement for use in determining the autonomic balance of the patient. Various embodiments, for example, provide a combination of sensors to trend heart rate and/or respiration rate to provide an indicator of activity.

Two methods for detecting respiration involve measuring a transthoracic impedance and minute ventilation. Respiration can be an indicator of activity, and can provide an explanation of increased sympathetic tone. For example, it may not be appropriate to change or modify a treatment for modulating autonomic tone due to a detected increase in sympathetic activity attributable to exercise.

Respiration measurements (e.g. transthoracic impedance) can also be used to measure Respiratory Sinus Arrhythmia (RSA). RSA is the natural cycle of arrhythmia that occurs through the influence of breathing on the flow of sympathetic and vagus impulses to the sinoatrial node. The rhythm of the heart is primarily under the control of the vagus nerve, which inhibits heart rate and the force of contraction. The vagus nerve activity is impeded and heart rate begins to increase when a breath is inhaled. When exhaled, vagus nerve activity increases and the heart rate begins to decrease. The degree of fluctuation in heart rate is also controlled significantly by regular impulses from the baroreceptors (pressure sensors) in the aorta and carotid arteries. Thus, a measurement of autonomic balance can be provided by correlating heart rate to the respiration cycle.

Therapy Protocols

The present subject matter modulates autonomic tone using a cardiac or myocardial conditioning therapy with myocardial pacing component (CPPT) and a neural stimulation component. Preconditioning of the myocardium occurs as a prophylactic therapy in preparation for an anticipated event. For example, the myocardium can be preconditioned in anticipation for surgery, or can be preconditioned based on observed or detected events that indicate an increased probability of an upcoming ischemic event. Examples of such events include a previous myocardial infarction and angina. Prophylactic conditioning can be used to modulate autonomic tone from higher sympathetic tendencies toward an autonomic balance to improve the health of a patient prone to heart failure, hypertension and remodeling. Postconditioning of the myocardium occurs as a therapeutic therapy to a disease. For example, postconditioning of the myocardium can reduce the size of any infarct area caused by the ischemic event. For example, the postconditioning therapy can be triggered based on commands received from a patient or physician after observing a myocardial infarction, or a physician can deliver postconditioning therapy after a surgical procedure for which the heart was stopped. In an embodiment, the device detects an ischemic event or other event indicated for postconditioning therapy, and automatically delivers the postconditioning therapy. The postconditioning therapy can occur during the time of reperfusion, for a time after reperfusion, or during and for a time after reperfusion.

A cardiac conditioning therapy may also be referred to as a cardiac protective therapy, as it is protects against the deleterious effects of an autonomic tone with an undesirably high sympathetic tendency. The cardiac conditioning therapy may mimic the effects of exercise.

FIG. 1 illustrates the autonomic response to a period of exercise. Exercise is a stimulus that increases the sympathetic response. After the period of exercise ends, a reflex response to the exercise increases the parasympathetic tone. The parasympathetic response appears to be a reaction to the sympathetic action of exercise. Those of ordinary skill in the art will understand that the illustrated graph is a simple illustration. The horizontal axis represents time, and the vertical axis represents the autonomic tone. For simplicity, the value of the vertical axis corresponding to the horizontal axis represents the autonomic balance (the balance between the sympathetic and parasympathetic neural activity). Those of ordinary skill in the art will know that, over time, as the health of the heart improves and the autonomic balance improves by having a more parasympathetic tone, the horizontal axis (representing the autonomic balance) will trend more toward the parasympathetic tone. By way of an everyday example of exercise, it is noted that a runner's resting heart rate tends to lower as the runner's conditioning improves. This example indicates that running, which temporarily increases sympathetic tone as evidenced by an increased heart rate, will trend the autonomic balance of the runner toward a more parasympathetic tone.

As discussed further below, some embodiments of the present subject matter use a reflex template that is indicative of the parasympathetic reflex response to the CPPT to control timing and/or of the neural stimulation. According to some embodiments, this reflex template is based on the response of a general or specific population to CPPT, and is programmed into the device. According to some embodiments, the reflex template is capable of being determined for an individual patient by monitoring an ABI to detect a reflex response to the CPPT.

Figure 2:
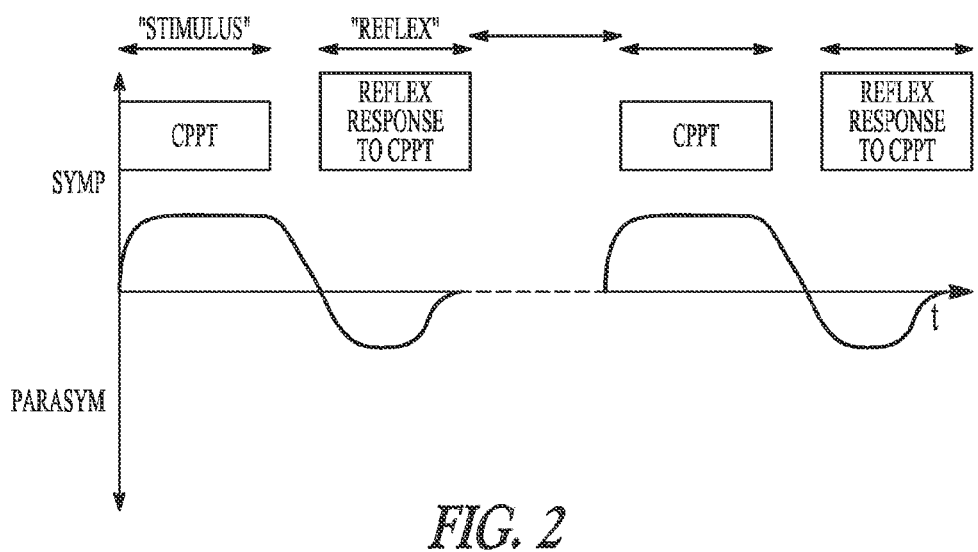
FIG. 2 illustrates the autonomic response to a period of cardiac protective pacing therapy (CPPT).

FIG. 2 illustrates the autonomic response to a period of CPPT. Similar to the period of exercise, CPPT is a stimulus the increases the sympathetic response during the period of pacing, and results in a reflex response that increases parasympathetic tone after the pacing ends. As illustrated, the CPPT functions as a stimulus that provides a sympathetic component (action) that generates a desired parasympathetic reflex (reaction to the action). A cardiac conditioning therapy may correspond to recommended exercises periods (e.g. 30 to 60 minutes, two times per day). Various therapy durations and frequencies can be used. Various cardiac conditioning therapies are programmed according to a schedule. Various cardiac conditioning therapies are programmed to occur after a detected period of exercise by the patient.

Figure 3:
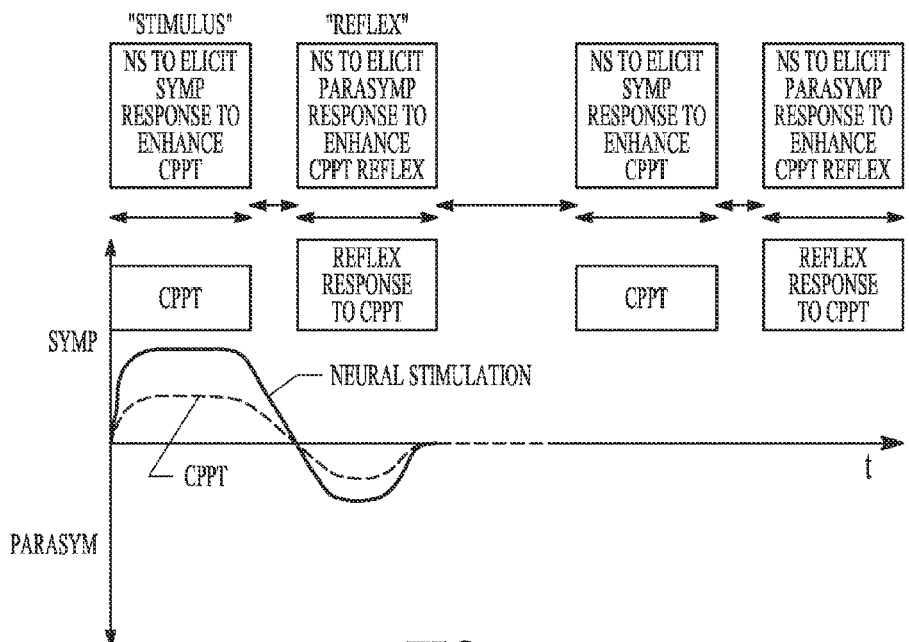
FIG. 3 illustrates, in general, the use of neural stimulation to enhance the parasympathetic reflex that results from the CPPT, according to various embodiments.

FIG. 3 illustrates, in general, the use of neural stimulation to enhance the parasympathetic reflex that results from the CPPT, according to various embodiments. Some embodiments deliver neural stimulation to elicit a sympathetic response during the pacing of the CPPT, to increase the sympathetic stimulus during the pacing of the CPPT, and to generate a larger parasympathetic response (a larger action results in a larger reaction). Some embodiments deliver neural stimulation to elicit a parasympathetic response after the pacing of the CPPT ends, to increase the parasympathetic response during the parasympathetic reflex resulting from the CPPT. Some embodiments deliver neural stimulation to both elicit a sympathetic response during the pacing of the CPPT and elicit a parasympathetic response after the pacing of the CPPT ends. In the illustrated graph of FIG. 3, the dotted line represents the autonomic tone attributable to CPPT, and the solid line represents, in a general fashion, the increased sympathetic tone attributable to neural stimulation during the CPPT period and the increased parasympathetic tone after the CPPT period.

According to various embodiments, the neural stimulation to elicit a sympathetic response includes neural stimulation to increase nerve traffic of a sympathetic nerve. According to various embodiments, the neural stimulation to elicit a sympathetic response includes neural stimulation to inhibit or decrease nerve traffic of a parasympathetic nerve. According to various embodiments, the neural stimulation to elicit a parasympathetic response includes neural stimulation to increase nerve traffic of a parasympathetic nerve. According to various embodiments, the neural stimulation to elicit a parasympathetic response includes neural stimulation to inhibit or decrease nerve traffic of a sympathetic nerve.

Some embodiments start the intermittent stress pacing therapy only after turning off the parasympathetic stimulation, and allowing a "wash out period" before turning on the intermittent stress pacing therapy. Some embodiments alternate the ON/OFF cycles of the intermittent stress pacing therapy and the parasympathetic therapy. For example, some embodiments schedule the therapy to predominantly deliver parasympathetic stimulation during day-time and intermittent stress pacing therapy during night. Various embodiments monitor exercise/activity or other sympathetic stimulation, start intermittent stress pacing therapy following the exercise/activity or other sympathetic stimulation, and after delivering the intermittent stress pacing therapy, delivering parasympathetic stimulation.

Figure 4A:
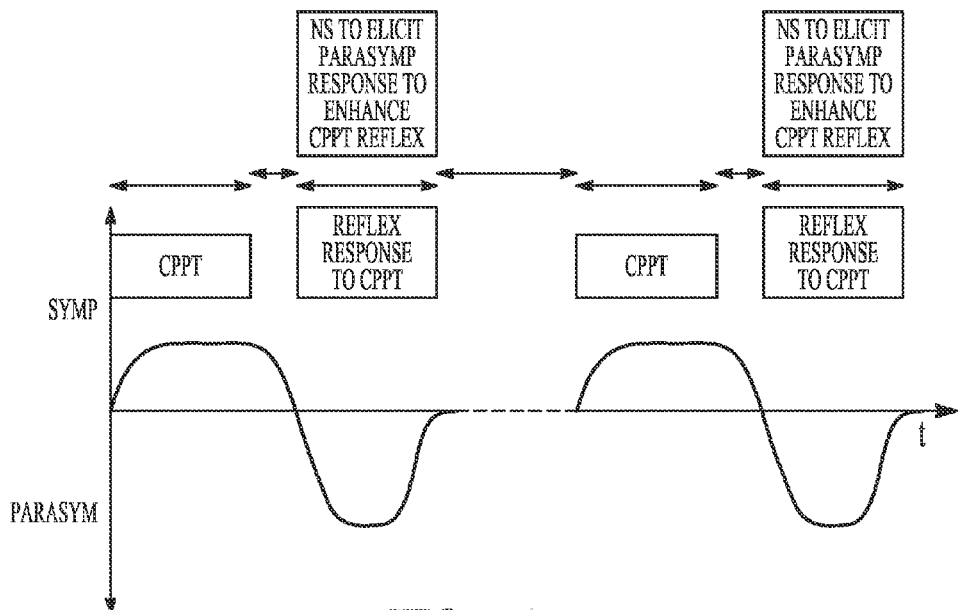
FIGS. 4A-F illustrate various embodiments that deliver neural stimulation timed to enhance the parasympathetic reflex by increasing the intensity of the parasympathetic response.
Figure 4B:
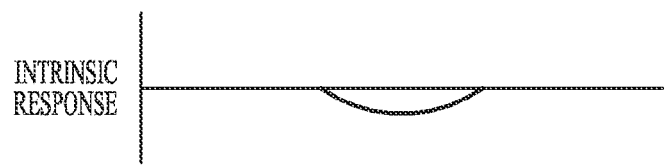
Figure 4C:
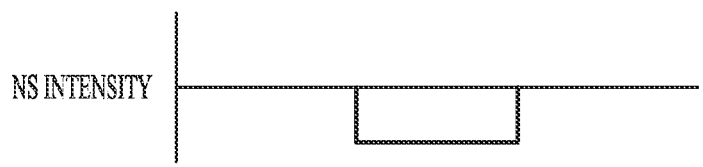
Figure 4D:
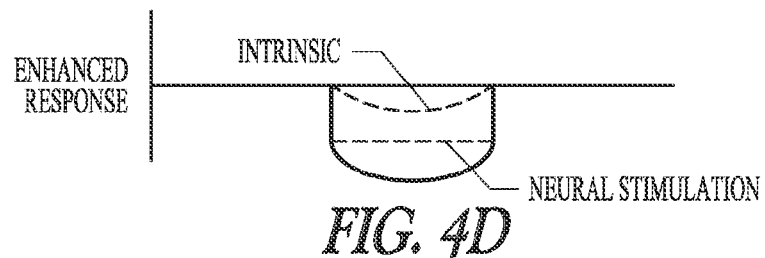
Figure 4E:
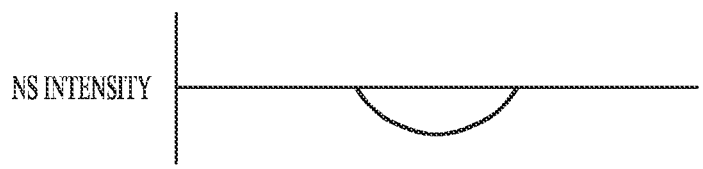
Figure 4F:
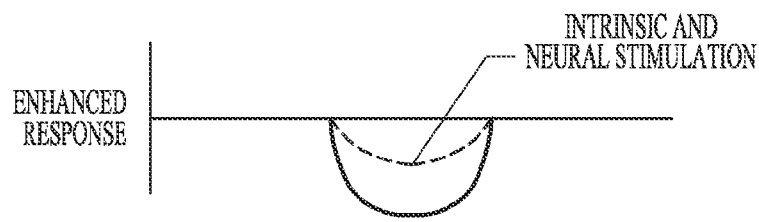

FIGS. 4A-F illustrate various embodiments that deliver neural stimulation timed to enhance the parasympathetic reflex by increasing the intensity of the parasympathetic response. In the illustrated embodiments, the neural stimulation is delivered with a steady or varied intensity during the reflex response to CPPT to enhance the parasympathetic response. FIG. 4A generally illustrates timing of CPPT and neural stimulation for an embodiment of the present subject matter. FIG. 4B illustrates the intrinsic or un-enhanced physiologic parasympathetic reflex response to CPPT, which is also illustrated as a dotted line in FIGS. 4D and 4F. A reflex template may correspond to this intrinsic response. FIG. 4C illustrates neural stimulation of a relatively steady intensity during the duration of the intrinsic response, which is also illustrated at a dotted line in FIG. 4D. FIG. 4D illustrates the parasympathetic response attributed to the neural stimulation of FIG. 4C and the intrinsic response, and illustrates a general offset of the intrinsic response toward a more parasympathetic tone. FIG. 4E illustrates neural stimulation where an intensity is varied to provide an intensity envelope similar to the intrinsic response illustrated in FIG. 4B. FIG. 4F illustrates the parasympathetic response attributed to the neural stimulation of FIG. 4E and the intrinsic response, and illustrates an enhanced response form that is generally a factor of the intrinsic response (e.g. 2 times the value of the intrinsic reflex response).

Figure 5:
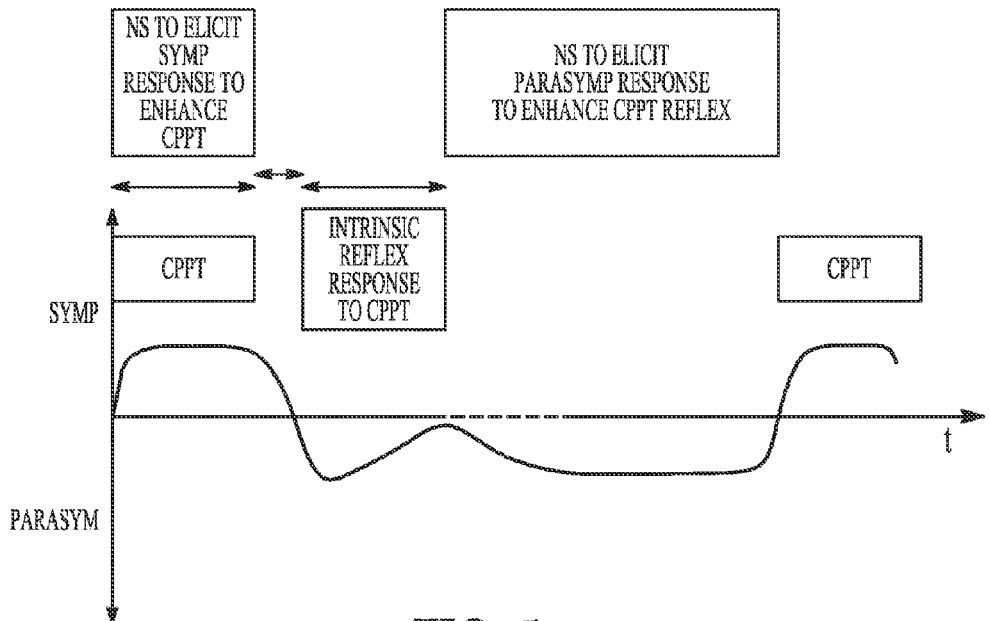
FIG. 5 illustrates various embodiments that deliver neural stimulation time to enhance the parasympathetic reflex by extending the duration of the parasympathetic response.

FIG. 5 illustrates various embodiments that deliver neural stimulation time to enhance the parasympathetic reflex by extending the duration of the parasympathetic response. In the illustrated embodiment, the neural stimulation is initiated after or near the end of the intrinsic response to CPPT. The timing may be based on a programmable delay based on a predetermined or a created reflex template. Thus, the neural stimulation can be timed to occur after a predetermined delay after the CPPT ends. Some embodiments also include neural stimulation to enhance the sympathetic stimulus during the CPPT period.

Figure 6:
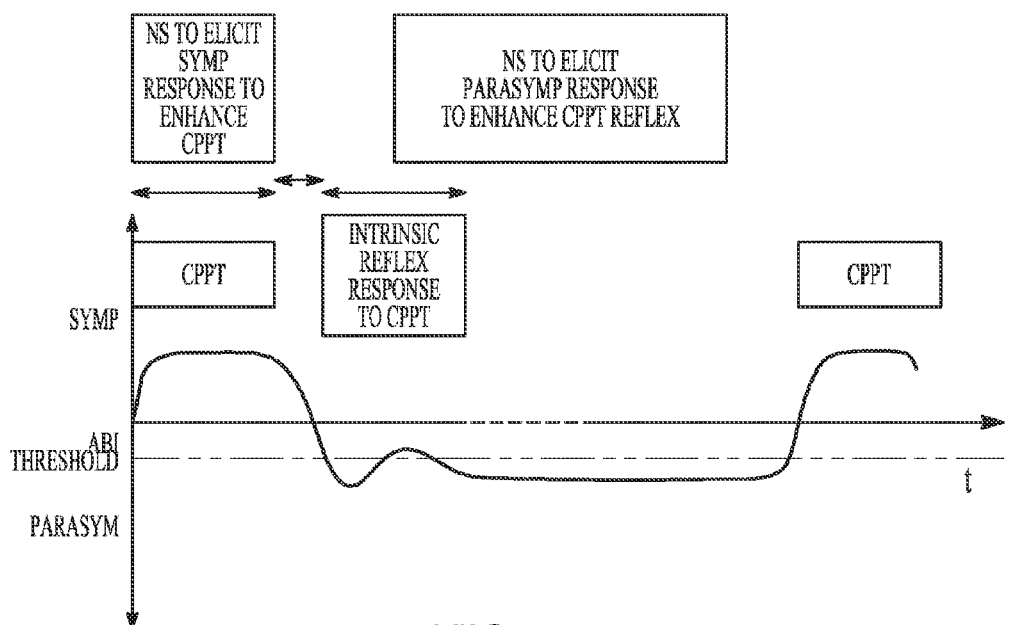
FIG. 6 illustrates various embodiments that deliver neural stimulation time to enhance the parasympathetic reflex by extending the duration of the parasympathetic response, where the neural stimulation is initiated when a monitored autonomic balance indicator (ABI) indicates that the autonomic tone has crossed an ABI threshold from a more parasympathetic tone toward a more sympathetic tone.

FIG. 6 illustrates various embodiments that deliver neural stimulation time to enhance the parasympathetic reflex by extending the duration of the parasympathetic response, where the neural stimulation is initiated when a monitored ABI indicates that the autonomic tone has crossed an ABI threshold from a more parasympathetic tone toward a more sympathetic tone. Thus, the timing of neural stimulation may be based on sensed parameter(s). Some embodiments base the timing on both sensed parameter(s) and programmable delay(s) (e.g. after a delay of x, initiate stimulation if/when threshold is crossed).

Figure 7A:
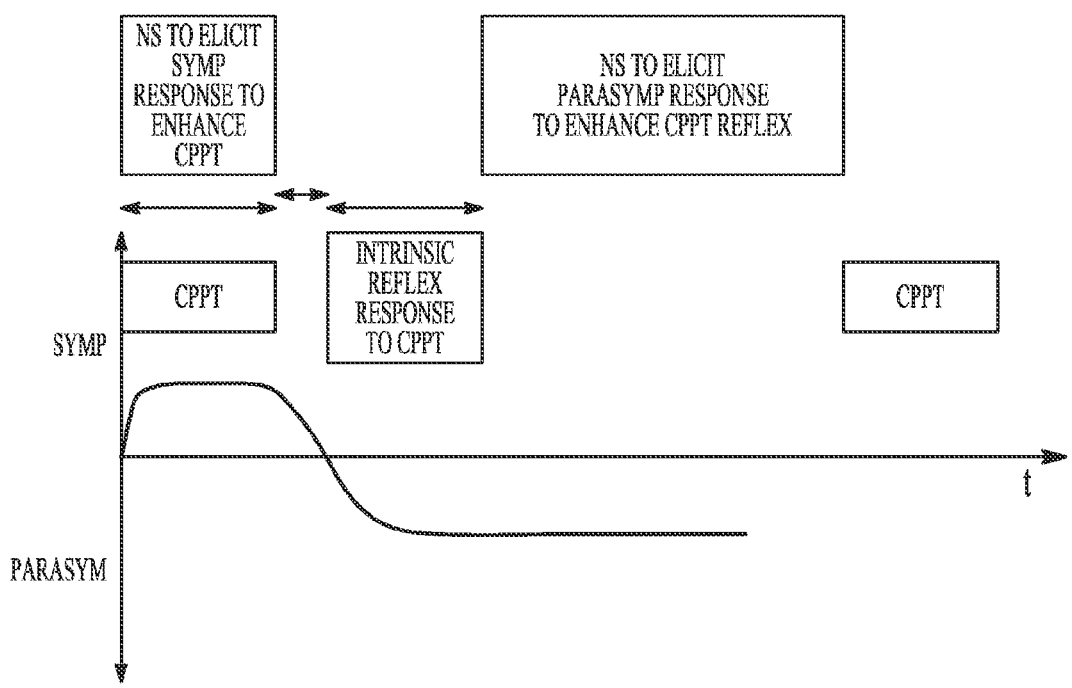
FIGS. 7A-E illustrate various embodiments that deliver neural stimulation timed to enhance the parasympathetic reflex by modulating the neural stimulation to provide an extended response.
Figure 7B:
Figure 7C:
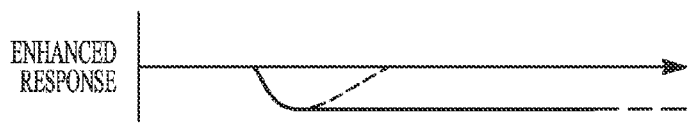
Figure 7D:
Figure 7E:

FIGS. 7A-F illustrate various embodiments that deliver neural stimulation timed to enhance the parasympathetic reflex by modulating the neural stimulation to provide an extended response. FIG. 7A generally illustrates timing of CPPT and neural stimulation for an embodiment of the present subject matter. FIG. 7B illustrates the intrinsic or un-enhanced physiologic parasympathetic reflex response to CPPT, which is also illustrated as a dotted line in FIGS. 7C-E. FIG. 7C illustrates an embodiment where the neural stimulation intensity is varied in a manner corresponding to the decay of the intrinsic response to provide a relatively steady parasympathetic tone during the neural stimulation. FIG. 7D illustrates an embodiment where the neural stimulation intensity is varied in a manner corresponding to the decay of the intrinsic response to provide a parasympathetic tone that slowly declines toward the autonomic balance during the neural stimulation. FIG. 7E illustrates an embodiment where the neural stimulation intensity is varied in a manner corresponding to the decay of the intrinsic response to provide a relatively steady parasympathetic tone during the neural stimulation that is less than a peak sympathetic tone that occurs during the intrinsic reflex response.

Figure 8:
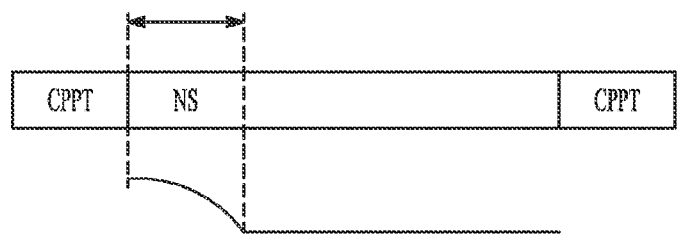
FIG. 8 illustrates a timing diagram of a therapy protocol according to various embodiments, such as is generally illustrated in FIG. 7C to provide a relatively steady parasympathetic tone attributed to both the intrinsic reflex response to the CPPT and the neural stimulation.

FIG. 8 illustrates a timing diagram of a therapy protocol according to various embodiments, such as is generally illustrated in FIG. 7C to provide a relatively steady parasympathetic tone attributed to both the intrinsic reflex response to the CPPT and the neural stimulation. In the embodiment illustrated in FIG. 8, the intensity of the neural stimulation ramps up to exponentially provide more intensity during the reflex template (reflex duration). After the time of the reflex, the illustrated embodiment provides neural stimulation of a relatively constant intensity to provide a relatively constant parasympathetic response.

Figure 9:
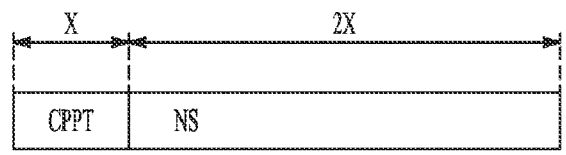
FIG. 9 illustrates a timing diagram of a therapy protocol according to various embodiments to increase the time of increased parasympathetic tone after the CPPT.

FIG. 9 illustrates a timing diagram of a therapy protocol according to various embodiments to increase the time of increased parasympathetic tone after the CPPT. In the embodiment illustrated in FIG. 9, the neural stimulation is delivered for a time period based on a function of the duration of the CPPT. In the illustrated embodiment, the neural stimulation to elicit a parasympathetic response begins when or shortly after the CPPT ends, and the duration of the neural stimulation is twice as long as the duration of the CPPT.

Preconditioning & Postconditioning Protocols

Figure 10A:
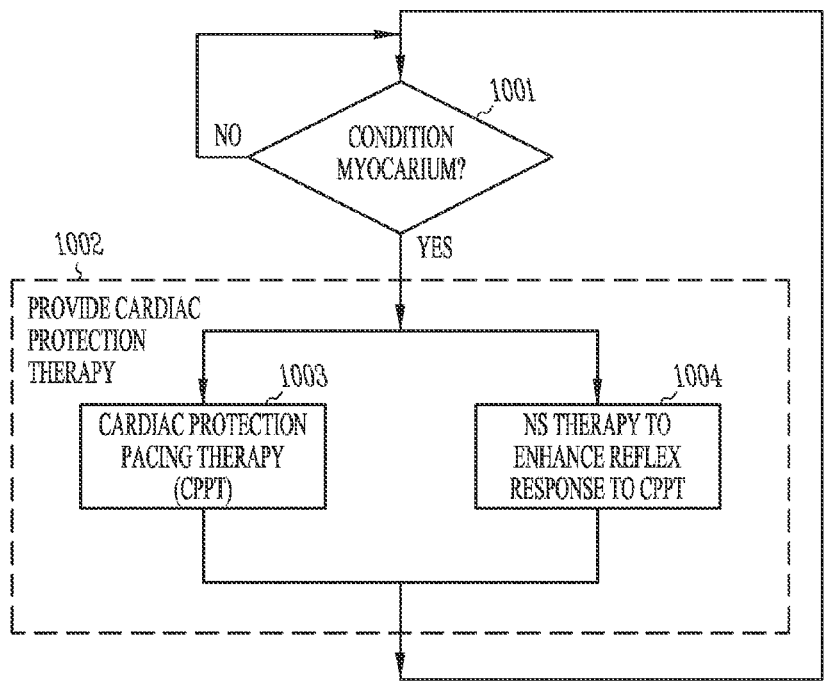
FIGS. 10A-10C illustrate methods for providing pacing and parasympathetic stimulation therapies to condition myocardium, according to various embodiments of the present subject matter.
Figure 10B:
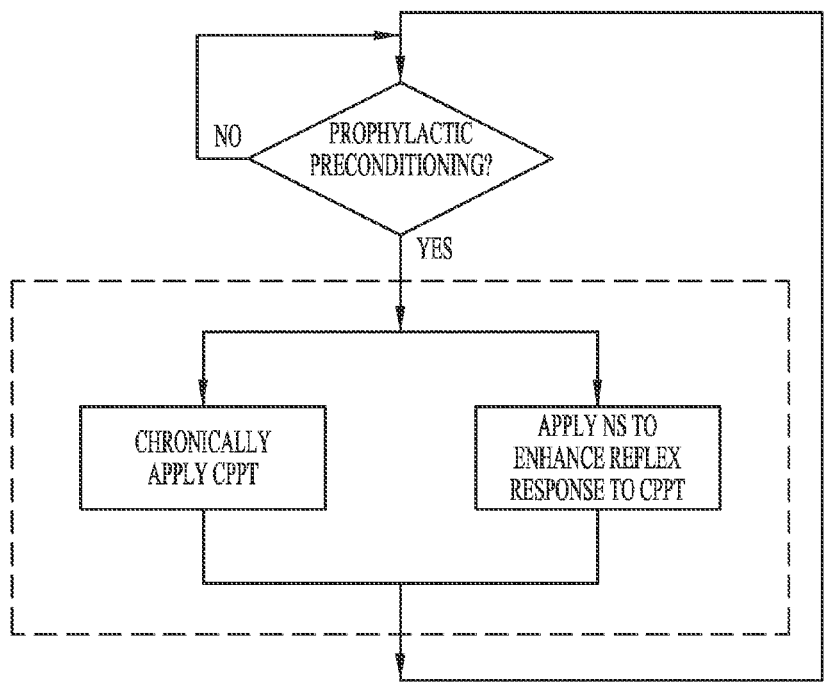
Figure 10C:
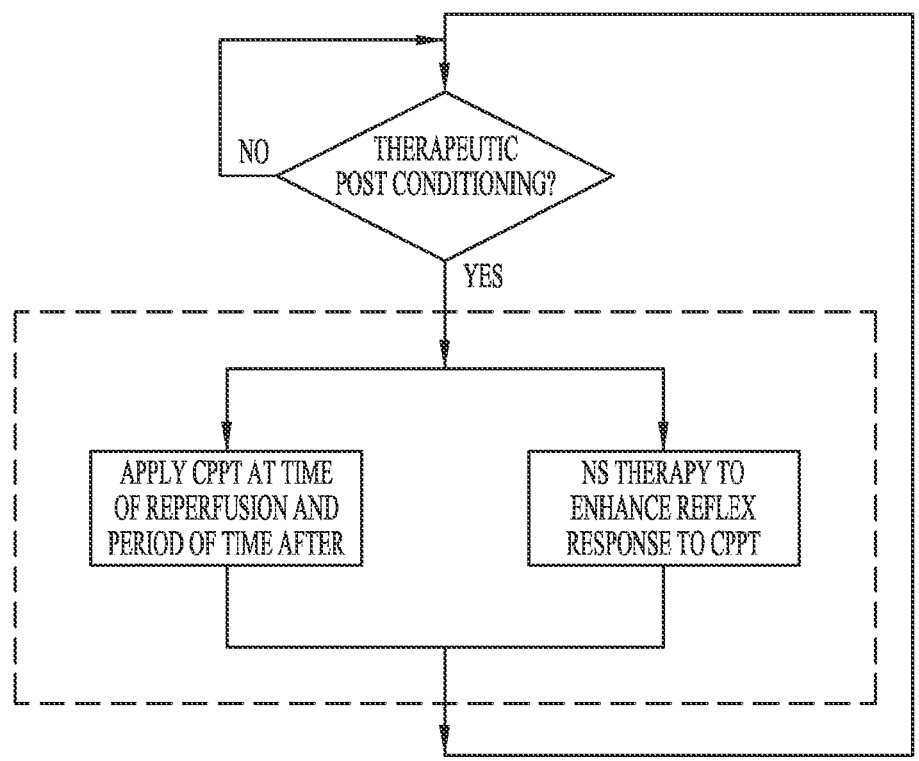

FIGS. 10A-10C illustrate methods for providing pacing and parasympathetic stimulation therapies to condition myocardium, according to various embodiments of the present subject matter. As illustrated in FIG. 10A, it is determined at 1001 whether to implement a therapy to condition myocardium. Once it is determined to condition myocardium, the process proceeds to provide a cardiac protection therapy at 1002. The therapy 1002 includes CPPT, illustrated at 1003, and neural stimulation therapy, illustrated at 1004. The therapies 1003 and 1004 are appropriately timed to enhance the reflex response to the CPPT.

FIG. 10B illustrates a method for providing pacing and parasympathetic stimulation therapies to provide prophylactic preconditioning therapy of the myocardium. Reasons for initiating a prophylactic preconditioning therapy include improving autonomic balance to reduce a risk for developing a disease, preparation for a surgical procedure, or an expected ischemic event due to sensed or known risk factors. As illustrated in FIG. 10B, both the CPPT and the neural stimulation therapy are chronically applied because of sensed (e.g. ABI) or known risk factors, according to various embodiments.

FIG. 10C illustrates a method for providing pacing and parasympathetic stimulation therapies to provide therapeutic postconditioning therapy of the myocardium. Reasons for initiating a therapeutic therapy include part of a surgical process for reperfusing the myocardium, a sensed or observed myocardial infarction, or any other sensed ischemic event. As illustrated in FIG. 10C, both the CPPT and neural stimulation are applied during at least a portion of reperfusion and for a period of time after the reperfusion of the myocardium, according to various embodiments.

Device Examples

Figure 11:
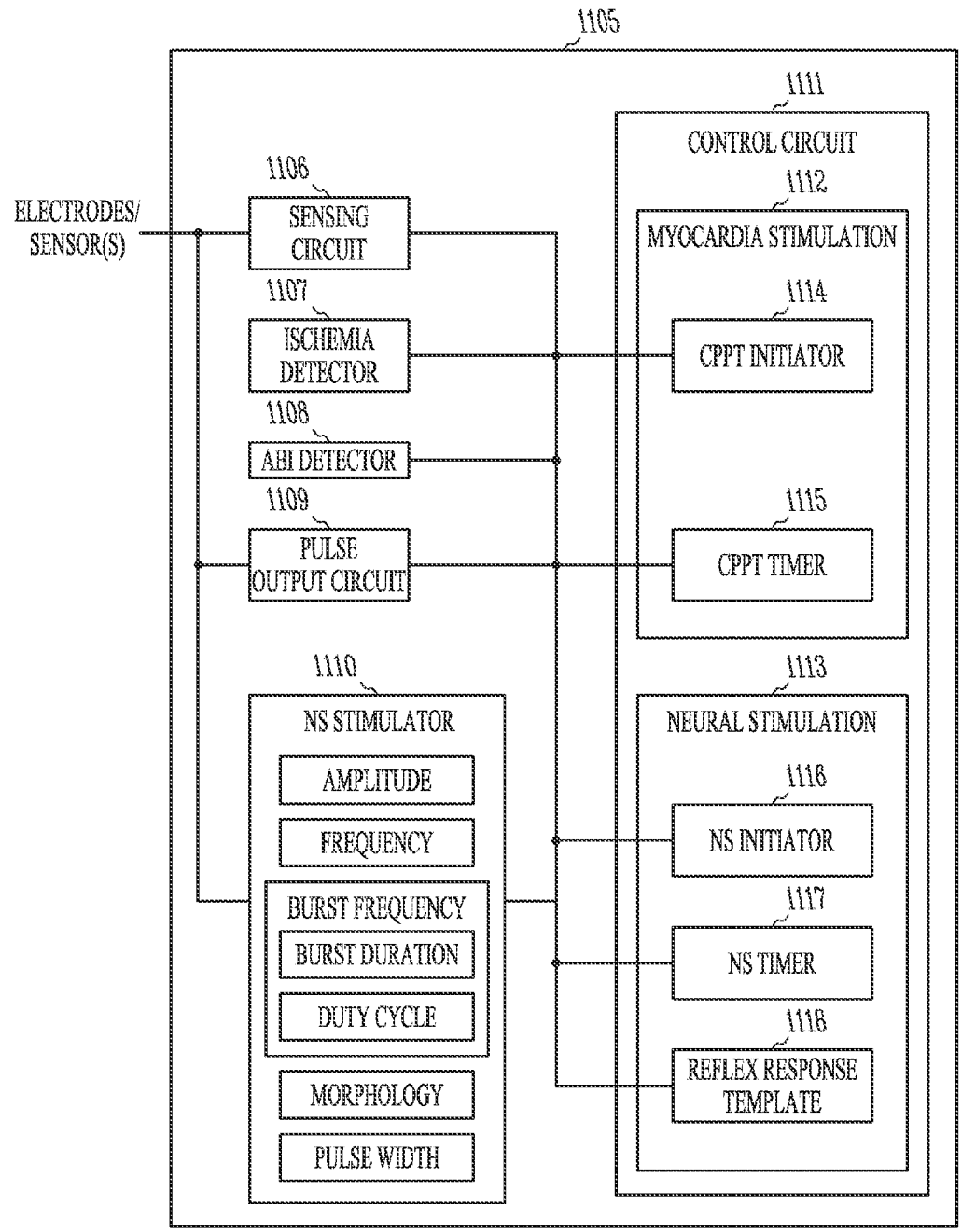
FIG. 11 illustrates a device embodiment for providing pacing and neural stimulation therapies to condition myocardium, according to various embodiments of the present subject matter.

FIG. 11 illustrates a device embodiment for providing pacing and neural stimulation therapies to condition myocardium, according to various embodiments of the present subject matter. The illustrated device 1105 includes a sensing circuit 1106, an ischemia detector 1107, and ABI detector 1108, a pulse output circuit 1109, a neural stimulator 1110, and a control circuit 1111. Sensing circuit 1106 senses one or more signals using a number of electrodes and/or one or more sensors. The one or more signals are indicative of ABI and/or ischemic events. ABI detector 1108 determines the ABI from the signals. Ischemia detector 1107 determines the ischemic events from the signals. Pulse output circuit 1109 delivers myocardial pacing pulses to the heart, and neural stimulator 1110 provides neural stimulation to elicit a desired parasympathetic response (e.g. simulating a parasympathetic neural network) that innervates the heart, such as a vagus nerve, a branch of the vagus nerve, or a cardiac fat pad, or inhibiting an appropriate sympathetic network. Control circuit 1111 controls the delivery of the pacing pulses and neural stimulation based on one or more sensed signals and/or in response to the detected ABI and/or ischemic event. In various embodiments, the device 1105 is substantially contained in an implantable housing of implantable medical device.

The control circuit 1111 includes a myocardial stimulation module 1112 and a neural stimulation module 1113. The myocardial stimulation module 1112 includes a CPPT initiator 1114 and a CPPT timer 1115. CPPT initiator 1114 initiates one or more pacing sequences in accordance with a schedule and/or in response to an ABI and/or ischemic event. The CPPT sequences each include alternating pacing and non-pacing periods. The pacing periods each have a pacing duration during which a plurality of pacing pulse is delivered. The non-pacing periods each have a non-pacing duration during which no pacing pulse is delivered. Once CPPT is initiated, CPPT timer 1115 times that sequence. For example, various embodiments provide pacing for 10 minutes of every hour or for 30-60 minutes one or more times per day. These values are examples, and generally correspond to an exercise regimen. Those of ordinary skill in the art will understand that these values can be adjustable and programmable, according to various embodiments, to fit the particular needs of a patient. Various events can also be sensed and used as an input to time the stimulation at desired times. Examples of sensors to detect such events include activity sensors. A particular schedule may also be used, where the conditioning therapy is overridden (e.g. canceled or suspended) based on the sensed parameters. The neural stimulation module 1113 includes a neural stimulation initiator 1116, a neural stimulation timer 1117, and a reflex response template 1118. Neural stimulation initiator 1116 initiates one or more neural stimulation sequences according to a schedule and/or in response to a detected ABI. The one or more neural stimulation sequences each include alternating stimulation and non-stimulation periods. The stimulation periods each have a duration during which neural stimulation is delivered to a neural target to elicit a parasympathetic response (e.g. to stimulate a parasympathetic neural target or inhibit a sympathetic neural target). The non-stimulation periods each have a non-stimulation duration during which no neural stimulation is delivered. Once a neural stimulation sequence is initiated, neural stimulation timer 1117 times that sequence. For example, various embodiments provide neural stimulation (e.g. 300 μs pulses at 1-2 mA) for 10 seconds every minute. The reflex response template may be pre-programmed based on a generally known reflex for a population, or may be recorded based on monitored ABI in response to CPPT. This reflex response template is used, according to various embodiments, to control the duration and/or intensity of the neural stimulation. According to various embodiments, the neural stimulator circuitry 1110 includes modules to set or adjust any one or any combination of two or more of the following pulse features: the amplitude of the stimulation pulse, the frequency of the stimulation pulse, the burst frequency of the pulse, the wave morphology of the pulse, and the pulse width. The illustrated burst frequency pulse feature includes burst duration and duty cycle, which can be adjusted as part of a burst frequency pulse feature or can be adjusted separately without reference to a steady burst frequency. Such adjustments can be used to adjust the intensity of the neural stimulation to reduce or enhance the adjustments to the autonomic tone.

The neural stimulator may use electrodes to delivery electrical stimulation to a neural target. These neural electrodes can be on the same lead or on different leads as the cardiac pacing electrodes, depending on the locations of the desired parasympathetic neural target. Some embodiments use other techniques to deliver other energy to stimulate the neural target. For example, some embodiment use transducers to produce ultrasound or light energy waves to stimulate the neural target. Some embodiments use leadless "satellite" electrodes/transducers.

Figure 12:
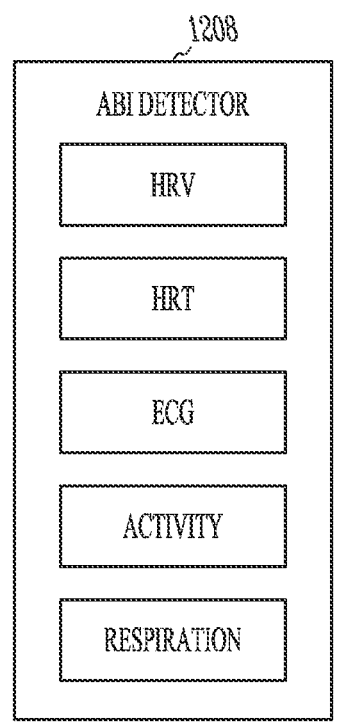
FIG. 12 illustrates an ABI detector, such as may be used in FIG. 11, according to various embodiments.

FIG. 12 illustrates an ABI detector 1208, such as may be used at 1108 in FIG. 11, according to various embodiments. The illustrated ABI detector includes detector(s) for HRV, HRT, ECG, activity and respiration. As identified earlier, one or more of these may be used to provide an ABI. For example, HRT and HRV may both be used to provide a composite parameter, and activity can be used to provide context (e.g. apparent rise in sympathetic tone is attributed to a period of exercise) for the composite parameter.

Figure 13:
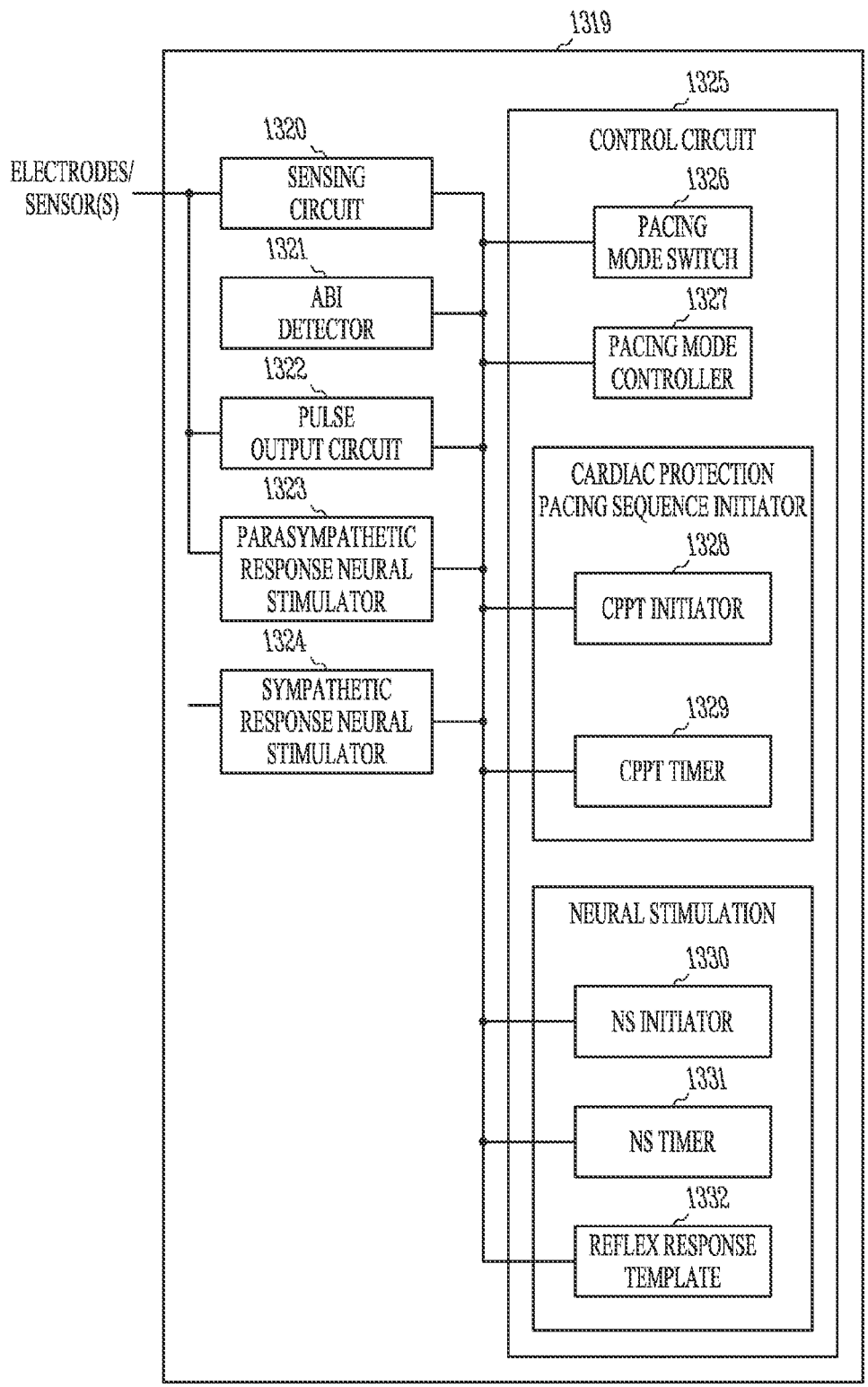
FIG. 13 illustrates a device embodiment for providing pacing and neural stimulation to condition myocardium, according to various embodiments of the present subject matter.

FIG. 13 illustrates a device embodiment for providing pacing and neural stimulation to condition myocardium, according to various embodiments of the present subject matter. The illustrated device 1319 includes sensing circuit 1320, ABI detector 1321, pulse output circuit 1322, a parasympathetic response neural stimulator 1323, a sympathetic response neural stimulator 1324, and a control circuit 1325. Sensing circuit 1320 senses the one or more signals indicative of the autonomic health of the patient. ABI detector 1321 detects the ABI from the one or more signals. Pulse output circuit 1322 delivers the pacing pulses to heart. Control circuit 1325 controls the delivery of the pacing pulses and neural stimulation based on the one or more sensed signals and/or in response to the ABI. In some embodiments, the control circuit controls the delivery of the pacing pulses and neural stimulation in an open loop control (i.e. no feedback). Some embodiments, the delivery of pacing pulses and neural stimulation is delivered using feedback from the ABI detector or sensing circuit. In various embodiments, the device is substantially contained in an implantable housing of implantable medical device.

Control circuit 1325 includes a pacing mode switch 1326, a pacing mode controller 1327, a CPPT initiator 1328 to initiate a CPPT period, and a CPPT timer 1329 to control the duration of the CPPT period. Control circuit 1325 allows the device to control the delivery of the cardiac protection therapy (pacing and neural stimulation) as well as other pacing therapies. This allows the function of CPPT pacing to be included in an implantable medical device that delivers pacing therapies on a long-term basis, such as for treatment of bradycardia and heart failure. In various embodiments, CPPT includes a temporary pacing therapy delivered for one or more brief periods according to a schedule and/or in response to an ABI, and the implantable medical device also delivers a chronic pacing therapy such as a bradycardia pacing therapy, or CRT. In other embodiments, the CPPT is the only pacing therapy delivered, or the CPPT is the only pacing therapy programmed to be delivered for at least a certain period of time.

Each pacing therapy is delivered by delivering pacing pulses in accordance with a predetermined pacing mode. Pacing mode switch 1326 switches the pacing mode from a chronic pacing mode to a temporary pacing mode when a CPPT sequence is initiated and to switch the pacing mode from the temporary pacing mode to the chronic pacing mode when the cardiac protection pacing sequence is completed. Pacing mode controller 1327 controls the delivery of the pacing pulses from pulse output circuit 1322 according to the pacing mode as selected by pacing mode switch 1326. The temporary pacing mode refers to the pacing mode used in a CPPT, which is a temporary pacing therapy. The chronic pacing mode refers to the pacing mode used in a chronic pacing therapy such as a bradycardia pacing therapy, or CRT. In one embodiment, the temporary pacing mode is substantially different from the chronic pacing mode, such that the cardiac protection pacing therapy changes the distribution of stress in the myocardium, thereby triggering the intrinsic myocardial protective mechanism against ischemic damage to the myocardial tissue.

CPPT initiator 1328 initiates one or more pacing sequences and neural stimulation initiator initiates one or more neural stimulation sequences according to a schedule, or in response to a command from a physician or patient or a determined ABI. In one embodiment, CPPT initiator 1328 also initiates one or more cardiac protection sequences in response to one or more commands issued by the user through external system.

In one embodiment, control circuit 1325 detects an arrhythmia and suspends the one or more cardiac protection pacing sequences in response to the detection of the arrhythmia. Control circuit 1325 includes an arrhythmia detector to detect one or more predetermined types of arrhythmia. In one embodiment, CPPT initiator cancels, holds, or otherwise adjusts the timing of the initiation of a cardiac protection sequence in response to a detection of arrhythmia. In one embodiment, CPPT timer terminates or suspends a pacing sequence in response to the detection of an arrhythmia that occurs during the sequence.

The illustrated control circuit also includes a neural stimulation initiator 1330 to control the timing of neural stimulation using the parasympathetic response neural stimulator 1323 and/or the sympathetic response neural stimulator 1324, a neural stimulation timer 1331 to time the neural stimulation for use to control the neural stimulation, and a reflex response template 1332 used to control the intensity and/or duration of the neural stimulation.

Figure 14:
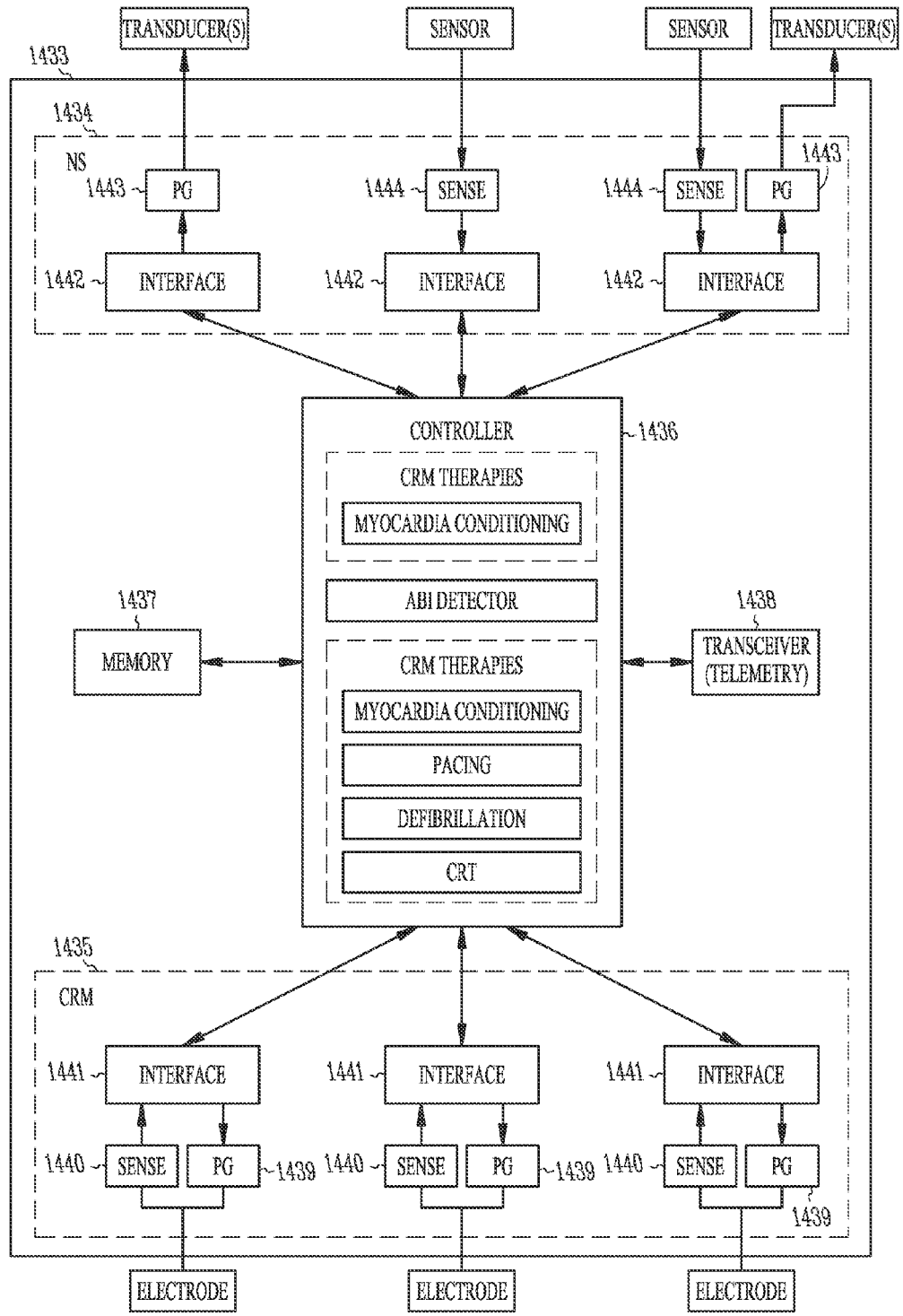
FIG. 14 illustrates an implantable medical device (IMD) having a neural stimulation (NS) component and cardiac rhythm management (CRM) component, according to various embodiments of the present subject matter.

FIG. 14 illustrates an implantable medical device (IMD) 1433 having a neural stimulation (NS) component 1434 and cardiac rhythm management (CRM) component 1435, according to various embodiments of the present subject matter. The illustrated device includes a controller 1436 and memory 1437. According to various embodiments, the controller includes hardware, software, or a combination of hardware and software to perform the neural stimulation and CRM functions. For example, the programmed therapy applications discussed in this disclosure are capable of being stored as computer-readable instructions embodied in memory and executed by a processor. According to various embodiments, the controller includes a processor to execute instructions embedded in memory to perform the neural stimulation and CRM functions. CRM functions include myocardial conditioning (CPPT). Other examples of CRM functions include bradycardia pacing, antitachycardia therapies such as antitachycardia pacing and defibrillation, and CRT. The controller also executes instructions to detect ABI and/or ischemia. The illustrated device further includes a transceiver 1438 and associated circuitry for use to communicate with a programmer or another external or internal device. Various embodiments include a telemetry coil.

The CRM therapy section 1435 includes components, under the control of the controller, to stimulate a heart and/or sense cardiac signals using one or more electrodes. The CRM therapy section includes a pulse generator 1439 for use to provide an electrical signal through an electrode to stimulate a heart, and further includes sense circuitry 1440 to detect and process sensed cardiac signals. An interface 1441 is generally illustrated for use to communicate between the controller 1436 and the pulse generator 1439 and sense circuitry 1440. Three electrodes are illustrated as an example for use to provide CRM therapy. However, the present subject matter is not limited to a particular number of electrode sites. Each electrode may include its own pulse generator and sense circuitry. However, the present subject matter is not so limited. The pulse generating and sensing functions can be multiplexed to function with multiple electrodes.

The NS therapy section 1434 includes components, under the control of the controller, to stimulate a neural stimulation target and in some embodiments sense parameters associated with nerve activity or surrogates of nerve activity such as blood pressure and respiration. Three interfaces 1442 are illustrated for use to provide neural stimulation. However, the present subject matter is not limited to a particular number interfaces, or to any particular stimulating or sensing functions. Pulse generators 1443 are used to provide electrical pulses to transducer or transducers for use to stimulate a neural stimulation target. According to various embodiments, the pulse generator includes circuitry to set, and in some embodiments change, the amplitude of the stimulation pulse, the frequency of the stimulation pulse, the burst frequency of the pulse, and the morphology of the pulse such as a square wave, triangle wave, sinusoidal wave, and waves with desired harmonic components or other signals. Sense circuits 1444 are used to detect and process signals from a sensor, such as a sensor of nerve activity, blood pressure, respiration, and the like. The interfaces 1442 are generally illustrated for use to communicate between the controller 1436 and the pulse generator 1443 and sense circuitry 1444. Each interface, for example, may be used to control a separate lead. Various embodiments of the NS therapy section only include a pulse generator to stimulate neural targets such as a vagus nerve.

Figure 15:
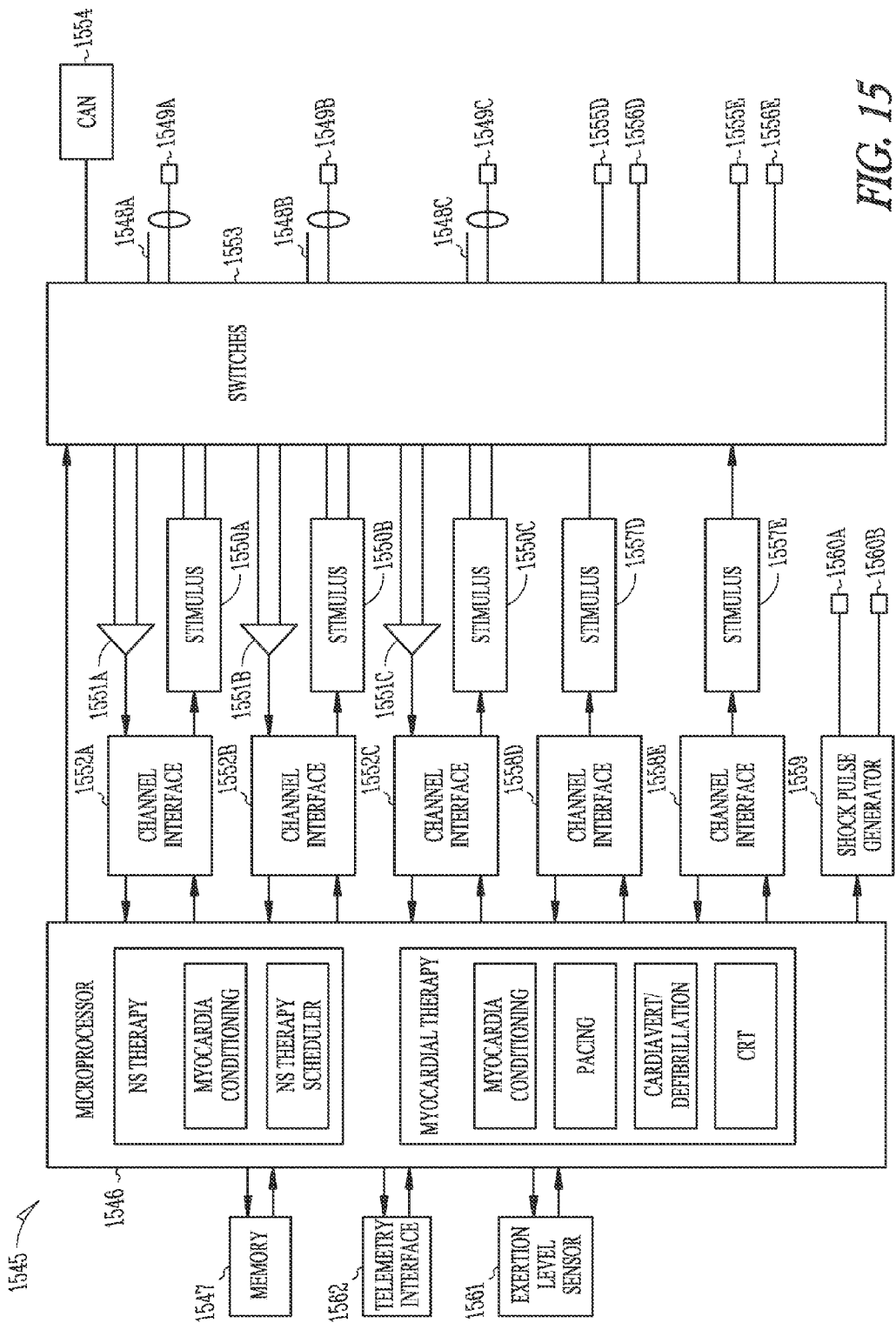
FIG. 15 shows a system diagram of an embodiment of a microprocessor-based implantable device.

FIG. 15 shows a system diagram of an embodiment of a microprocessor-based implantable device. The device 1545 is equipped with multiple sensing and pacing channels which may be physically configured to sense and/or pace multiple sites in the atria or the ventricles, and to provide neural stimulation. The illustrated device can be configured for myocardial stimulation (e.g. myocardium conditioning pacing, bradycardia pacing, defibrillation, CRT) and neural stimulation (e.g. myocardium conditioning neural stimulation). The multiple sensing/pacing channels may be configured, for example, with one atrial and two ventricular sensing/pacing channels for delivering biventricular resynchronization therapy, with the atrial sensing/pacing channel used to deliver the biventricular resynchronization therapy in an atrial tracking mode as well as to pace the atria if required. The controller 1546 of the device is a microprocessor which communicates with memory 1547 via a bidirectional data bus. The controller could be implemented by other types of logic circuitry (e.g., discrete components or programmable logic arrays) using a state machine type of design. As used herein, the term "circuitry" should be taken to refer to either discrete logic circuitry or to the programming of a microprocessor.

Shown in FIG. 15, by way of example, are three sensing and pacing channels, such as can be used to provide myocardial stimulation/pacing, designated "A" through "C" comprising bipolar leads with ring, or proximal, electrodes 1548A-C and distal, or tip, electrodes 1549A-C, pulse generators 1550A-C, sensing amplifiers 1551A-C, and channel interfaces 1552A-C. Each channel thus includes a pacing channel made up of the pulse generator connected to the electrode and a sensing channel made up of the sense amplifier connected to the electrode. The channel interfaces 1552A-C communicate bidirectionally with the microprocessor 1546, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing, and the intrinsic atrial and/or ventricular rates can be detected by measuring the time intervals between atrial and ventricular senses, respectively. The pacing algorithms also include the appropriate preconditioning and postconditioning pacing algorithms.

The electrodes of each bipolar lead are connected via conductors within the lead to a switching network 1553 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring, or proximal, and tip, or distal, electrodes of a lead or in a unipolar mode using only one of the electrodes of the lead with the device housing or can 1554 serving as a ground electrode.

Also shown in FIG. 15, by way of example, are nerve stimulation channels designated "D" and "E." Neural stimulation channels are incorporated into the device. These channels can be used to deliver neural stimulation to elicit a parasympathetic and/or sympathetic response as part of a cardioprotective therapy, as discussed in this document. The illustrated channels include leads with electrodes 1555D and 1556D and electrodes 1555E and 1556E, a pulse generator 1557D and 1557E, and a channel interface 1558D and 1558E. The illustrated bipolar arrangement is intended as a non-exclusive example. Other neural stimulation electrode arrangements are within the scope of the present subject matter. Other embodiments may use unipolar leads in which case the neural stimulation pulses are referenced to the can or another electrode. The pulse generator for each channel outputs a train of neural stimulation pulses which may be varied by the controller as to amplitude, frequency, duty-cycle, pulse duration, and wave morphology, for example. A shock pulse generator 1559 is also interfaced to the controller for delivering a defibrillation shock via a pair of shock electrodes 1560A and 1560B to the atria or ventricles upon detection of a shockable tachyarrhythmia.

The illustrated controller includes a module for controlling neural stimulation (NS) therapy and module for controlling myocardial therapy. As illustrated, the NS therapy module includes a module for performing myocardial conditioning (e.g. vagal nerve stimulation or stimulation of a cardiac fat pad). Also as illustrated, the myocardial therapy module includes a module for controlling myocardial conditioning pacing, a module for controlling bradycardia pacing therapies, a module for controlling defibrillation therapies, and a module for controlling CRT. The illustrated neural stimulation therapy module includes a myocardial conditioning module and a neural stimulation scheduling module. The neural stimulation controlled by the myocardial conditioning module enhances the parasympathetic reflex from the CPPT delivered by the myocardial therapy module. The scheduler controls the timing and duration of the stimulation. The controller controls the overall operation of the device in accordance with programmed instructions stored in memory, including controlling the delivery of paces via the pacing channels, interpreting sense signals received from the sensing channels, and implementing timers for defining escape intervals and sensory refractory periods. The controller is capable of operating the device in a number of programmed pacing modes which define how pulses are output in response to sensed events and expiration of time intervals. Most pacemakers for treating bradycardia are programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity such that a pacing pulse is delivered to a heart chamber during a cardiac cycle only after expiration of a defined escape interval during which no intrinsic beat by the chamber is detected. Escape intervals for ventricular pacing can be restarted by ventricular or atrial events, the latter allowing the pacing to track intrinsic atrial beats. CRT is most conveniently delivered in conjunction with a bradycardia pacing mode where, for example, multiple excitatory stimulation pulses are delivered to multiple sites during a cardiac cycle in order to both pace the heart in accordance with a bradycardia mode and provide pre-excitation of selected sites. An exertion level sensor 1561 (e.g., an accelerometer, a minute ventilation sensor, or other sensor that measures a parameter related to metabolic demand) enables the controller to adapt the pacing rate in accordance with changes in the patient's physical activity and can enable the controller to modulate the delivery of neural stimulation and/or cardiac pacing. A telemetry interface 1562 is also provided which enables the controller to communicate with an external programmer or remote monitor.

System Examples

Figure 16:
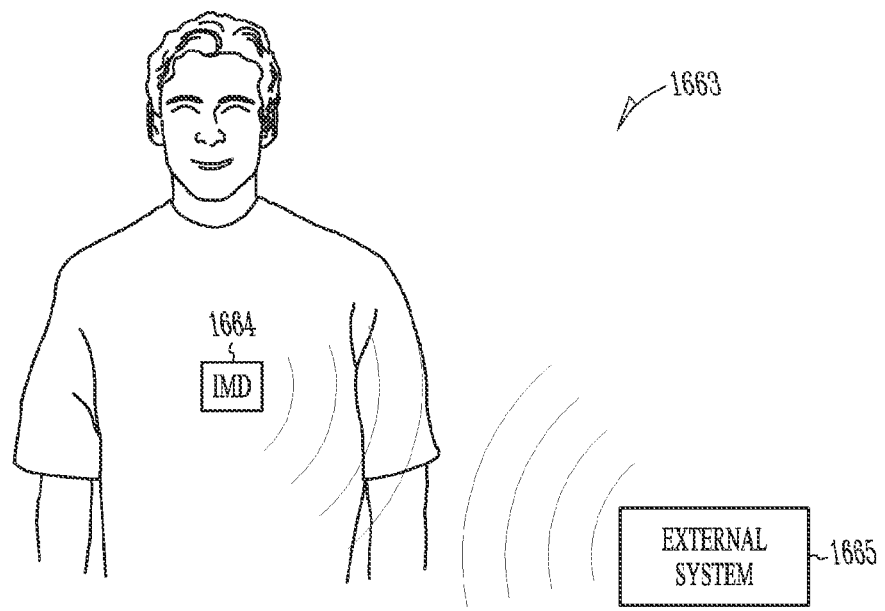
FIG. 16 illustrates a system including an implantable medical device (IMD) and an external system or device, according to various embodiments of the present subject matter.

FIG. 16 illustrates a system 1663 including an implantable medical device (IMD) 1664 and an external system or device 1665, according to various embodiments of the present subject matter. Various embodiments of the IMD include a combination of NS and CRM functions. The IMD may also deliver biological agents and pharmaceutical agents. The external system and the IMD are capable of wirelessly communicating data and instructions. In various embodiments, for example, the external systems and IMD use telemetry coils to wirelessly communicate data and instructions. Thus, the programmer can be used to adjust the programmed therapy provided by the IMD, and the IMD can report device data (such as battery and lead resistance) and therapy data (such as sense and stimulation data) to the programmer using radio telemetry, for example. The IMD stimulates a neural target and paces myocardium as part of the myocardium conditioning therapy.

In one embodiment, in addition to the CPPT, the MD also delivers one or more other cardiac pacing therapies, such a bradycardia pacing therapy, and CRT. If another pacing therapy is being delivered when a cardiac protection pacing sequence is to be initiated, that pacing therapy is temporarily suspended to allow the delivery of the CPPT and resumed upon completion of the CPPT sequence.

External system allows a user such as a physician or other caregiver or a patient to control the operation of IMD and obtain information acquired by the IMD. In one embodiment, external system includes a programmer communicating with the MD bi-directionally via a telemetry link. In another embodiment, the external system is a patient management system including an external device communicating with a remote device through a telecommunication network. The external device is within the vicinity of the IMD and communicates with IMD bi-directionally via a telemetry link. The remote device allows the user to monitor and treat a patient from a distant location. The patient monitoring system is further discussed below.

The telemetry link provides for data transmission from implantable medical device to external system. This includes, for example, transmitting real-time physiological data acquired by IMD, extracting physiological data acquired by and stored in IMD, extracting therapy history data stored in implantable medical device, and extracting data indicating an operational status of IMD (e.g., battery status and lead impedance). Telemetry link also provides for data transmission from external system to IMD. This includes, for example, programming IMD to acquire physiological data, programming IMD to perform at least one self-diagnostic test (such as for a device operational status), and programming IMD to deliver at least one therapy.

Figure 17:
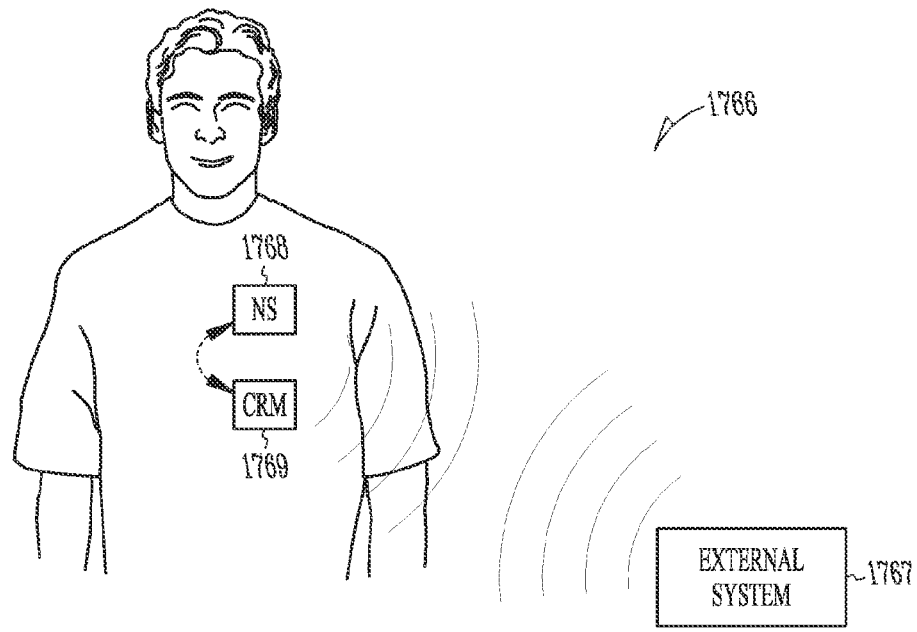
FIG. 17 illustrates a system including an external device, an implantable neural stimulator (NS) device and an implantable cardiac rhythm management (CRM) device, according to various embodiments of the present subject matter.

FIG. 17 illustrates a system 1766 including an external device 1767, an implantable neural stimulator (NS) device 1768 and an implantable cardiac rhythm management (CRM) device 1769, according to various embodiments of the present subject matter. Various aspects involve communicating between an NS device and a CRM device or other cardiac stimulator. The NS device delivers neural stimulation for a myocardium conditioning therapy, and the CRM device delivers CPPT for the myocardium conditioning therapy. In various embodiments, this communication allows one of the devices to time the therapy (i.e. enhance reflex response to CPPT) based on data received from the other device. Some embodiments provide on-demand communications. The illustrated NS device and the CRM device are capable of wirelessly communicating with each other, and the external system is capable of wirelessly communicating with at least one of the NS and the CRM devices. For example, various embodiments use telemetry coils to wirelessly communicate data and instructions to each other. In other embodiments, communication of data and/or energy is by ultrasonic means. Rather than providing wireless communication between the NS and CRM devices, various embodiments provide a communication cable or wire, such as an intravenously-fed lead, for use to communicate between the NS device and the CRM device.

Figure 18:
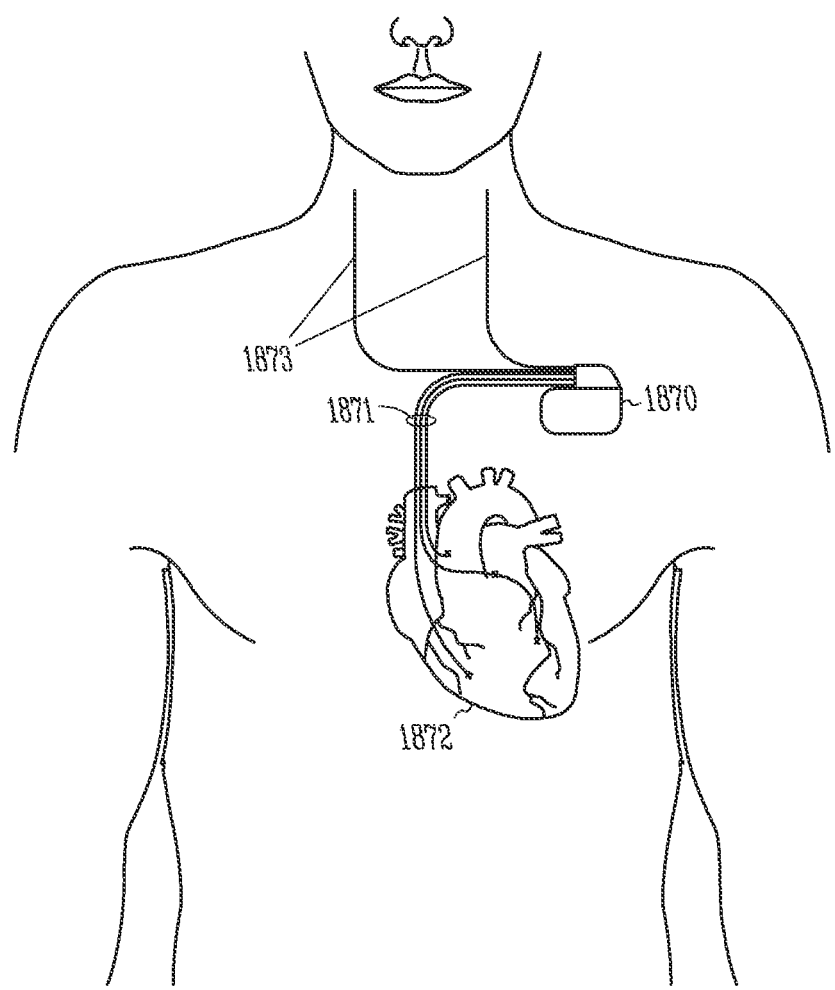
FIG. 18 illustrates an IMD embodiment placed subcutaneously or submuscularly in a patient's chest with lead(s) positioned to provide a CRM therapy to a heart, and with lead(s) positioned to stimulate a vagus nerve.

FIG. 18 illustrates an IMD 1870 placed subcutaneously or submuscularly in a patient's chest with lead(s) 1871 positioned to provide a CRM therapy to a heart 1872, and with lead(s) 1873 positioned to stimulate a vagus nerve, by way of example and not by way of limitation. The leads 1871 can be used to deliver the myocardium pacing to condition myocardium. The leads 1871 are positioned in or proximate to the heart to provide a desired CPPT. In some embodiments, lead(s) are positioned in or proximate to the heart to provide a desired defibrillation therapy, a desired CRT therapy, or a combination thereof. According to various embodiments, neural stimulation lead(s) 1873 are subcutaneously tunneled to a neural target, and can have a nerve cuff electrode to stimulate the neural target. Some lead embodiments are intravascularly fed into a vessel proximate to the neural target, and use transducer(s) within the vessel to transvascularly stimulate the neural target. For example, some embodiments stimulate the vagus using electrode(s) positioned within the internal jugular vein. Two neural stimulation leads are illustrated as stimulating left and right vagus nerves. The present subject matter is not limited to stimulation of both vagus nerves.

Figure 19:
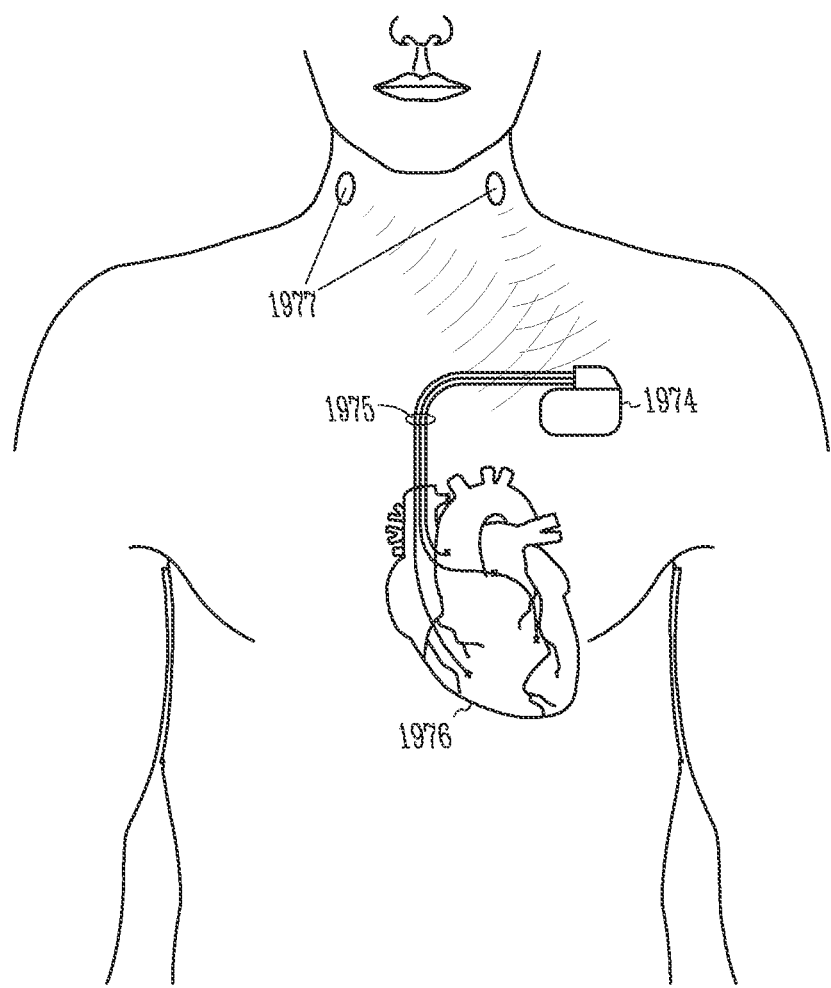
FIG. 19 illustrates an IMD embodiment with lead(s) positioned to provide a CRM therapy to a heart, and with satellite transducers positioned to stimulate at least one parasympathetic neural target as part of a myocardium conditioning therapy.

FIG. 19 illustrates an IMD 1974 with lead(s) 1975 positioned to provide a CRM therapy to a heart 1976, and with satellite transducers 1977 positioned to stimulate at least one parasympathetic neural target as part of a myocardium conditioning therapy. The satellite transducers are connected to the IMD, which functions as the planet for the satellites, via a wireless link. Stimulation and communication can be performed through the wireless link. Examples of wireless links include RF links and ultrasound links. Although not illustrated, some embodiments perform myocardial stimulation using wireless links. Examples of satellite transducers include subcutaneous transducers, nerve cuff transducers and intravascular transducers.

Figure 20:
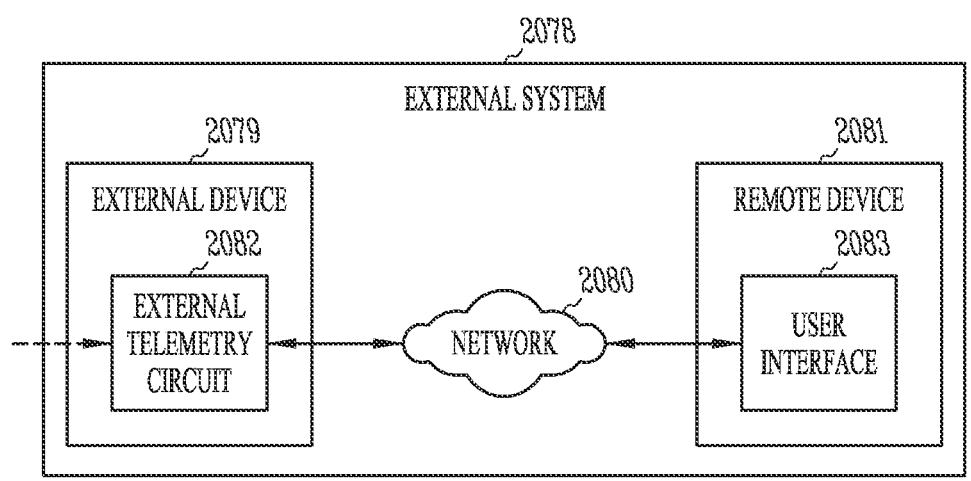
FIG. 20 is a block diagram illustrating an embodiment of an external system.

The external system illustrated in FIGS. 16 and 17 includes a programmer, in some embodiments, and includes a patient management system in other embodiments. FIG. 20 is a block diagram illustrating an embodiment of an external system 2078. As illustrated, external system 2078 is a patient management system including an external device 2079, a telecommunication network 2080, and a remote device 2081. External device 2079 is placed within the vicinity of an IMD and includes external telemetry system 2082 to communicate with the IMD. Remote device(s) 2081 is in one or more remote locations and communicates with external device 2079 through network 2080, thus allowing a physician or other caregiver to monitor and treat a patient from a distant location and/or allowing access to various treatment resources from the one or more remote locations. In one embodiment, remote device 2081 includes a user interface 2083. This allows the user to initiate and/or adjust the cardiac protection pacing therapy.

The systems can be designed to stimulate nerve traffic (providing a parasympathetic response when the vagus is stimulated), or to inhibit nerve traffic (providing a sympathetic response when the vagus is inhibited). Various embodiments deliver unidirectional stimulation or selective stimulation of some of the nerve fibers in the nerve. According to various embodiments, the device, as illustrated and described above, is adapted to deliver neural stimulation as electrical stimulation. Other elements for delivering neural stimulation can be used. For example, some embodiments use transducers to deliver neural stimulation using other types of energy, such as ultrasound, light, magnetic or thermal energy.

One of ordinary skill in the art will understand that, the modules and other circuitry shown and described herein can be implemented using software, hardware, and combinations of software and hardware. As such, the terms module and circuitry, for example, are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods are implemented using a computer data signal embodied in a carrier wave or propagated signal, that represents a sequence of instructions which, when executed by one or more processors cause the processor(s) to perform the respective method. In various embodiments, the methods are implemented as a set of instructions contained on a computer-accessible medium capable of directing a processor to perform the respective method. In various embodiments, the medium is a magnetic medium, an electronic medium, or an optical medium.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method, comprising:
    intermittently delivering a sympathetic stimulus, including delivering a sequence of stress-inducing pacing pulses adapted to increase sympathetic tone during the stress-inducing pacing, the sequence of stress-inducing pacing resulting in a parasympathetic reflex after the sequence of stress-inducing pacing; and
    delivering neural stimulation to elicit a parasympathetic response in a coordinated manner with respect to the sequence of stress-inducing pacing pulses to enhance the parasympathetic reflex after the sequence of stress-inducing pacing, including timing the neural stimulation to elicit the parasympathetic response after the sequence of stress-inducing pacing pulses and concurrent with at least a portion of the parasympathetic reflex to the sequence of stress-inducing pacing to enhance a parasympathetic effect of the parasympathetic reflex.

2. The method of claim 1, further comprising adjusting the neural stimulation and timing the adjustments to provide a desired parasympathetic tone resulting in the parasympathetic response and the parasympathetic reflex.

3. The method of claim 1, further comprising controlling the neural stimulation using a reflex template representative of the parasympathetic response after the sequence of stress-inducing pacing.

4. The method of claim 1, further comprising delivering neural stimulation to elicit a sympathetic response in a coordinated manner with respect to the sequence of stress-inducing pacing pulses to enhance the parasympathetic reflex after the sequence of stress-inducing pacing, including timing the sympathetic response during the sequence of stress-inducing pulses to provide a larger sympathetic stimulus, resulting in an enhanced parasympathetic reflex in response to the larger sympathetic stimulus.

5. The method of claim 1, wherein delivering a sequence of stress-inducing pacing pulses includes at least one of:
    pacing at a rate faster than a rate of an intrinsic cardiac rhythm without the pacing pulse; or
    pacing a ventricle with at least one of:
        an AV delay that is shorter than an AV delay of an intrinsic cardiac rhythm without the pacing pulses; or
        a VV delay that is longer than a VV delay of the intrinsic cardiac rhythm without the pacing pulses.

6. A method, comprising:
    intermittently delivering a sympathetic stimulus, including delivering a sequence of stress-inducing pacing pulses adapted to increase sympathetic tone during the stress-inducing pacing, the sequence of stress-inducing pacing resulting in a parasympathetic reflex after the sequence of stress-inducing pacing; and
    delivering neural stimulation to elicit a sympathetic response in a coordinated manner with respect to the sequence of stress-inducing pacing pulses to enhance the parasympathetic reflex after the sequence of stress-inducing pacing, including timing the neural stimulation to elicit the sympathetic response during the sequence of stress-inducing pulses to provide a larger sympathetic stimulus, resulting in an enhanced parasympathetic reflex in response to the larger sympathetic stimulus.

7. The method of claim 6, wherein delivering a sequence of stress-inducing pacing pulses includes at least one of:
    pacing at a rate faster than a rate of an intrinsic cardiac rhythm without the pacing pulse; or
    pacing a ventricle with at least one of:
        an AV delay that is shorter than an AV delay of an intrinsic cardiac rhythm without the pacing pulses; or
        a VV delay that is longer than a VV delay of the intrinsic cardiac rhythm without the pacing pulses.

* * * * *